United States Patent [19]
Faanes et al.

[11] Patent Number: 5,695,760
[45] Date of Patent: Dec. 9, 1997

[54] MODIFIED ANTI-ICAM-1 ANTIBODIES AND THEIR USE IN THE TREATMENT OF INFLAMMATION

[75] Inventors: Ronald Bertrand Faanes, Pound Ridge, N.Y.; Paul Edward McGoff, Watertown, Conn.; Bret Allen Shirley, New Milford, Conn.; David Stuart Scher, Danbury, Conn.

[73] Assignee: Boehringer Inglehiem Pharmaceuticals, Inc., Ridgefield, Conn.

[21] Appl. No.: 427,355

[22] Filed: Apr. 24, 1995

[51] Int. Cl.$^6$ .................. A61K 39/395; C07K 16/28
[52] U.S. Cl. ....................... 424/178.1; 424/181.1; 530/391.1; 530/388.85
[58] Field of Search .............. 530/391.1, 388.85; 424/181.1, 178.1

[56] References Cited

U.S. PATENT DOCUMENTS

| | | | |
|---|---|---|---|
| 4,179,337 | 12/1979 | Davis et al. | 435/181 |
| 4,371,520 | 2/1983 | Uemura et al. | 424/85 |
| 4,379,086 | 4/1983 | Kimura et al. | 260/112 |
| 4,649,115 | 3/1987 | Safai et al. | 435/240 |
| 4,692,331 | 9/1987 | Uemura et al. | 424/85 |
| 4,711,842 | 12/1987 | Taniyama et al. | 435/68 |
| 4,719,290 | 1/1988 | Curry et al. | 530/387 |
| 4,732,863 | 3/1988 | Tomasi et al. | 436/547 |
| 4,745,180 | 5/1988 | Moreland et al. | 530/351 |
| 4,791,192 | 12/1988 | Nakagawa et al. | 530/399 |
| 4,880,913 | 11/1989 | Doleschel et al. | 530/387 |
| 4,917,888 | 4/1990 | Katre et al. | 424/85.91 |
| 4,935,465 | 6/1990 | Garman | 525/54.1 |
| 5,091,176 | 2/1992 | Braatz et al. | 424/78.17 |
| 5,169,627 | 12/1992 | Cunningham-Rundles | 424/85.91 |
| 5,171,663 | 12/1992 | Basta et al. | 435/7.1 |
| 5,252,714 | 10/1993 | Harris et al. | 530/391.9 |
| 5,283,317 | 2/1994 | Saifer et al. | 528/405 |
| 5,284,931 | 2/1994 | Springer . | |
| 5,286,852 | 2/1994 | Osther et al. | 530/388.35 |
| 5,304,595 | 4/1994 | Rhee et al. | 525/54.1 |
| 5,308,626 | 5/1994 | Landucci et al. | 424/93 |
| 5,336,603 | 8/1994 | Capon et al. | 435/69.7 |
| 5,342,940 | 8/1994 | Ono et al. | 544/218 |
| 5,349,052 | 9/1994 | Delgado et al. | 530/351 |
| 5,356,633 | 10/1994 | Woodle et al. | 424/450 |

OTHER PUBLICATIONS

Hauq et al. Transplantation 55: 766–773, 1993.
Kitamura Cancer Research 51: 4310–4315 1991.
Wilkinson, Immunology Letters 15: 17–22, 1987.
Matsushima, Biochemistry International 26: 485–490, 1992.
Shaltiel, Methods Enzymology 104: 69–96, 1984.
Saitoh, H., *Japanese J. of Allergology*:43 579–584 (1994).
Budnick, A. et al., "Proteolytic Cleavage is the Mechanism Responsible for the Production of Soluble ICAM–1 Molecules by Human Keratinocytes" *J. Invest. Derm.* 102: 566 (1994).
Rothlein, R. et al., "Generation and Characterization of an Anti–Idiotypic Antibody Specific for Intercellular Adhesion Molecule–1" *Intl. Arch. Allerg. Immunol.* 100: 121–127 (1993).
Wang, J.H. et al., "In vivo Treatment with Anti–ICAM–1 Anti–LFA–1 Antibodies Inhibits Contact Sensitization Induced Migration of Epidermal Langerhans Cells to Regional Lymph Nodes" *FASEB J.* 8: A745 (1994)FASEB J. 8: A981 (1994).
Dinda, P.K. et al., "Effect of Anti–CD18 and Anti–ICAM–1 Monoclonal Antibodies (MAb) On Ethanol(eth)–Induced Jejunal Mucosal Injury" *Gastroenterol.* 106: A230 (1994).
Herold, K.C. et al., "Prevention of Autoimmune Diabetes by Treatment with Anti–LFA–1 and Anti–ICAM–1 Monoclonal Antibodies" *Clin. Res.* 42: 119A (1994).
Zeng, Y. et al., "Prolongation of Human Pancreatic Islet Xenografts by Pretreatment of Islets with Anti–Human ICAM–1 Monoclonal Antibody" *Transplant. Proceed.* 26: 1120 (1994).
Huang, Y.W. et al., "Cytotoxicity of a Novel Anti–ICAM–1 Immunotoxin on Human Myeloma Cell Lines" *Hybridoma* 12: 661–675 (1993).
Kelly, K.J. et al., "Antibody to Intercellular Adhesion Molecule–1 (ICAM–1) Protects the Kidney Against Ischemia" *J. Am. Soc. Nephrology* :4 738 (1993).
Archelos, J.J. et al., "Suppression of Experimental Allergic Neuritis by an Antibody to the Intercellular Adhesion Molecule ICAM–1" *Brain* 116: 1043–1058 (1993).
Zhang, R.L. et al., "Anti–ICAM–1 Antibody Reduces Ischemic Tissue Damage After Transient Middle Cerebral Artery Occlusion in Rat" *Stroke* 25: 266 (1994).
Bowes, M.P. et al., "Monoclonal Antibody to the ICAM–1 Adhesion Site Reduces Neurological Damage in a Rabbit Cerebral Embolism Stroke Model" *Exper. Neuro.* 119: 215–219 (1993).
Pavilack, M.A. et al., "Antibodies to ICAM–1 and LFA–1 in High–Risk Corneal Transplantation" *Invest. Opthalmol. Vis. Sci.* 35: 1896 (1994).
Kavanaugh, A.F. et al., "Treatment of Refractory Rheumatoid Arthritis with an Anti–CD54 (Intercellular Adhesion Molecule–1; ICAM–1) Monoclonal Antibody" *Arthritis Rheum.* 35: S43 (1992).
Kavanaugh, A.F. et al., "Pharmacokinetic Analysis of Rheumatoid Arthritis Patients Treated with an Anti–CD54 (Intercellular Adhesion Molecule–1; ICAM–1) Monoclonal Antibody" *Arthritis Rheum.* 35: S106 (1992).

(List continued on next page.)

*Primary Examiner*—Lila Feisee
*Assistant Examiner*—Nancy A. Johnson
*Attorney, Agent, or Firm*—Howrey & Simon; Jeffery L Auerbach

[57] ABSTRACT

Methods for preventing or treating inflammation are provided. Specifically, such inflammation can be effectively treated or prevented through the use of anti-ICAM-1 antibodies which have been modified to contain poly(ethylene) glycol adducts. The modification reduces the immunoreactivity of the antibodies, and thus increases the antibodies' serum half life. Methods for forming, purifying and using such modified antibodies are described.

31 Claims, 5 Drawing Sheets

OTHER PUBLICATIONS

Kavanaugh, A.F. et al., "Anti–CD54 (Intercellular Adhesion Molecule–1; ICAM–1) Monoclonal Antibody Therapy in Rheumatoid Arthritis" *Clin. Res.* 42: 314A (1994).

Kavanaugh, A.F. et al., "Anti–CD54 (Intercellular Adhesion Molecule–1; ICAM–1) Monoclonal Antibody Therapy in Refractory Rheumatoid Arthritis" *Arthritis Rheum.* 36: S40 (1993).

Schultze–Koops. H. et al., "Treatment of Rheumatoid Arthritis Patients with a Monoclonal Antibody to Intercellular Adhesion Molecule–1 (ICAM–1) Results in T Lymphocyte Hyporesponsiveness to in vitro Mitogenic Stimulation" *FASEB J.* 8: A745 (1994).

Omura, T. et al., "Accerlerated Rejection of Allografted Rat Liver Perfused with Anti–ICAM–1 Monoclonal Antibody" *Immunobiol.* 186: 241–245 (1992).

Kavanaugh, A.F. et al., "Anti–CD54 (Intercellular Adhesion Molecule–1; ICAM–1) Monoclonal Antibody Therapy in Refractory Rheumatoid Arthritis" *Allergy Clin. Immunol.* 91: 227 (1993).

Abuchowski, A. et al., "Cancer Therapy with Chemically Modified Enzymes. I. Antitumor Properties of Polyethylene Glycol–Asparaginase Conjugates" *Canc. Biochem. Biophys.* 7: 175–186 (1984).

Mast, A.E. et al., "Evaulation of the Rapid Plasma Elimination of Recombinant $\alpha_1$–Proteinase Inhibitor: Synthesis of Polyethylene Glycol Conjugates with Improved Therapeutic Potential" *J. Lab. Clin. Med.* 116: 58–65 (1990).

Nakayomi, K. et al., "Chemical Modification of Alpha–Thrombin and In Vitro Characterization of its Anticoagulant Activity" *Biochem. Intl.* 22: 75–84 (1990).

Sada, E. et al., "Resistance to Proteolysis of Antibody Ligands Modified with Polyethylene Glycol" *J. Ferment. Bioeng.* 71: 137–139 (1991).

Matsuyama, H. et al., "Phospholipase D Modified with a Polyethylene Glycol Derivative" *Chem. Pharm. Bull.* 39: 743–746 (1991).

Zalipsky, S. et al., "Evaluation of a New Reagent for Covalent Attachment of Polyethylene Glycol to Proteins" *Biotechnol. App. Biochem.* 15: 100–114 (1992).

Cameron, G.W. et al., "Introduction to Chromatographic Methods for Protein Purification" *Meth. Molec. Cell. Biol.* 4: 184:188 (1993).

Raymond, J. et al., "Hydrophobic Interaction Chromatography: A New Method for Sunflower Protein Fractionation" *J. Chromatogr.* 212: 199–209 (1981).

Ochoa, J.L. "Hydrophobic (interaction) Chromatography" *Biochimie.* 60: 1–15 (1978).

Roggenbuck, D. et al., "Purification and Immunochemical Characterization of a Natural Human Polyreactive Monoclonal IgM Antibody" *J. Immunol. Meth.* 167: 207–218 (1994).

Michaelson, S. et al., "High Performance Capillary Electrophoresis: Principles, Present Possibilities and Future Potentialities in Studies of Low and High Molecular Weight Charged and Uncharged Biomolecules" *Pol. J. Food Nutr. Sci.* 3/44: 5–44 (1994).

Rippel, G. et al., "Characterization of Stationary Phases Used in Reverse–Phase and Hydrophobic Interacton Chromatography" *J. Chromatogr.* 668: 301–312 (1994).

Szepesy, L. et al., "Effect of the Characteristics of the Phase System on the Retention of Proteins in Hydrophobic Interaction Chromatography" *J. Chromatogr.* 668: 337–344 (1994).

Huddleston, J.G. et al., "On the Use of Mild Hydrophobic Interaction Chromatography for 'Method Scouting' Protein Purification Strategies in Aqueous Two–Phase Systems: A Study Using Model Proteins" *Biotechnol. Bioeng.* 44: 626–635 (1994).

Watanabe, E. et al., "Selection of Chromatographic Protein Purification Operations Based on Physicochemical Properties" *Annals NY Acad. Sci.* 721: 348–364 (1994).

Karr, L.J., et al., "Use of Poly(ethylene Glycol)–Modified Antibody in Cell Extraction" *Methods in Enzymology* 228: 337–390 (Academic press, Ed. 1994).

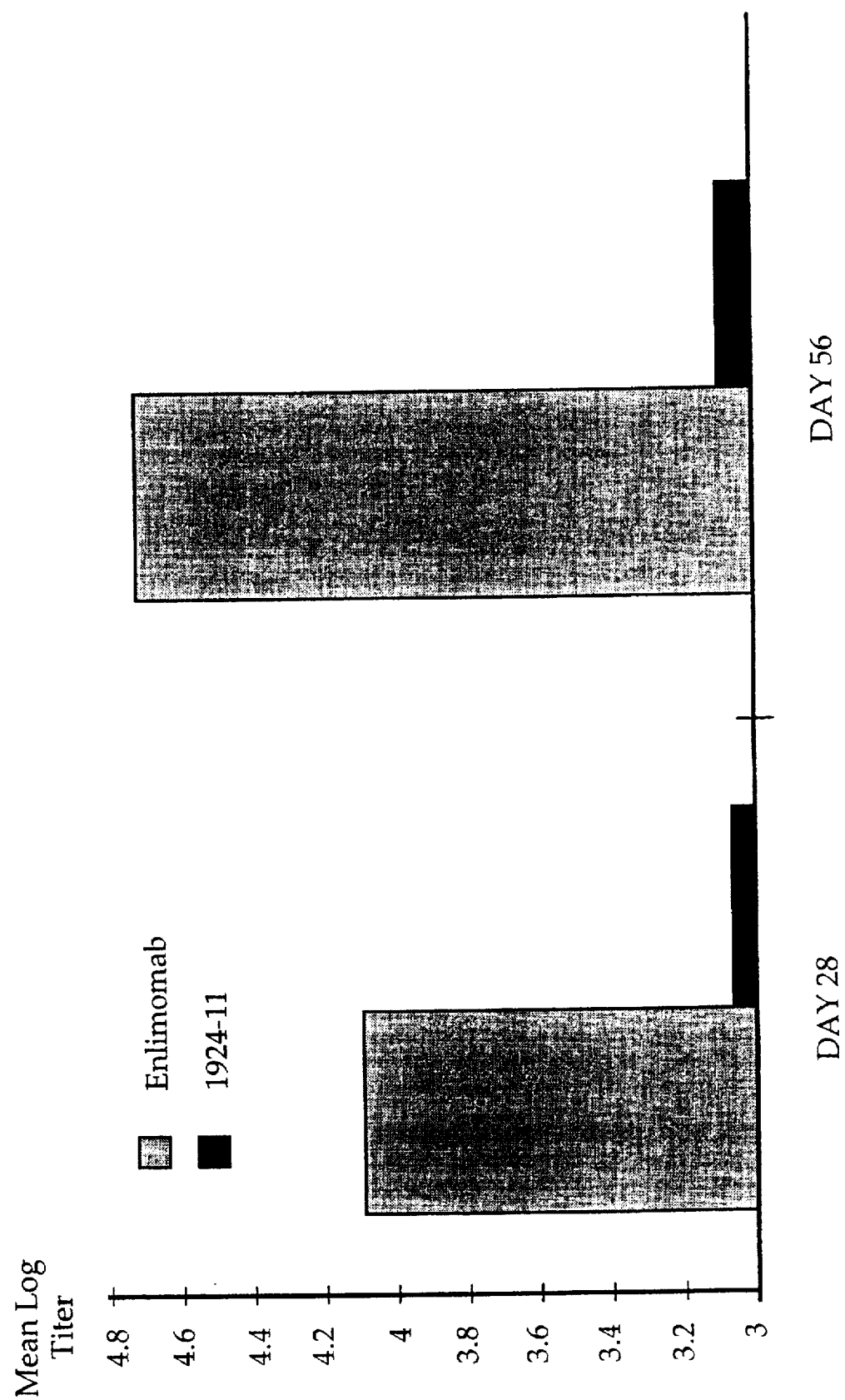

MODIFIED ANTI-ICAM-1 ANTIBODIES AND THEIR USE IN THE TREATMENT OF INFLAMMATION

FIELD OF THE INVENTION

The invention relates to modified antibodies that specifically bind to Intercellular Adhesion Molecule-1 ("ICAM-1"), and to the use of such molecules in the treatment of inflammation. More specifically, the invention concerns modified non-human anti-ICAM-1 antibodies that, as a consequence of such modification, exhibit improved therapeutic characteristics.

BACKGROUND OF THE INVENTION

I. Cellular Adhesion Molecules

In order to respond to infection and tissue damage, leukocytes must be able to migrate from the circulatory system to sites of ongoing inflammation. Such migration is accomplished by an adhesion phenomenon in which the leukocytes adhere to endothelial cells. Such cellular adhesion is also responsible for the attachment of leukocytes to antigen-presenting cells which occurs in the course of a normal specific immune system response. Cellular adhesion also permits leukocytes to attach to appropriate target cells so that lysis of virally-infected or tumor cells can occur.

Cellular adhesion has been found to be mediated by the binding interactions of endothelial cell surface receptors of the integrin family with leukocyte binding ligands of the super-immunoglobulin family (Springer, T. A., *Nature* 346:425–434 (1990); Smith, C. W., *Canad. J. Physiol. Pharmacol.* 71:76–87 (1993)).

A. The Cellular Adhesion Molecules Of The Integrin Family

The receptor molecules of the integrin family that are involved in cellular adhesion have been termed the "CD11/CD18 family of receptor molecules." These molecules were originally identified using hybridoma technology (Davignon, D. et al., *Proc. Natl. Acad. Sci. USA* 78:4535–4539 (1981); Springer, T. et al. *Eur. J. Immunol.* 9:301–306 (1979); Springer, T. et al., *Fed. Proc.* 44:2660–2663 (1985)).

The receptor molecules of the CD11/CD18 family are heterodimers containing an α subunit (CD11) and a β subunit (CD18) (Sanchez-Madrid, F. et al., *J. Exper. Med.* 158:1785–1803 (1983); Keizer, G. D. et al., *Eur. J. Immunol.* 15:1142–1147 (1985)). The β chain of the three molecules is identical. Although the α chains of the heterodimers differ, close analysis has revealed that there are substantial similarities between them. Reviews of the similarities between the α subunits of the LFA-1 related glycoproteins are provided by Sanchez-Madrid, F. et al., (*J. Exper. Med.* 158:586–602 (1983); *J. Exper. Med.* 158:1785–1803 (1983)).

The three different α subunits have been termed: CD11a (equivalently referred to as the LFA-1 α subunit), CD11b (equivalently referred to as the Mac-1 α subunit) and CD11c (equivalently referred to as the p150,95 α subunit) (Ruoslahti, E. et al., *Science* 238:491 (1987); Anderson, D. C. et al., *Ann. Rev. Med.* 38:175 (1987)).

The CD18 molecules were found to have a molecular weight of 95 kd whereas the molecular weights of the α chains were found to vary from 150 kd to 180 kd (Springer, T., *Fed. Proc.* 44:2660–2663 (1985)).

The CD11a/CD18 heterodimer is found on most lymphocytes (Springer, T. A., et al. *Immunol. Rev.* 68:111–135 (1982); Ruoslahti, E. et al., *Science* 238:491 (1987); Anderson, D. C. et al., *Ann. Rev. Med.* 38:175 (1987)). The CD11b/CD18 and CD11c/CD18 heterodimers are found on macrophages, granulocytes and large granular lymphocytes (Ruoslahti, E. et al., *Science* 238:491 (1987); Anderson, D. C. et al., *Ann. Rev. Med.* 38:175 (1987)). These three molecules play a role in cellular adhesion (Keizer, G. et al., *Eur. J. Immunol.* 15:1142–1147 (1985)).

The importance of the CD11a/CD18 complex and its cellular ligands in host defense has been illuminated by the identification of an autosomal recessive trait (designated "LAD" Syndrome for Leukocyte Adhesion Deficiency Syndrome) characterized by recurrent, severe bacterial infections in which affected individuals are unable to synthesize normal CD18 molecules (Ruoslahti, E. et al., *Science* 238:491 (1987); Anderson, D. C. et al., *Ann. Rev. Med.* 38:175 (1987); Anderson, D. C., et al., *Fed. Proc.* 44:2671–2677 (1985); Anderson, D. C., et al., *J. Infect. Dis.* 152:668–689 (1985)). Leukocytes from LAD patients display in vitro defects similar to normal counterparts whose LFA-1 family of molecules had been antagonized by antibodies. Furthermore, these individuals are unable to mount a normal immune response due to an inability of their cells to adhere to cellular substrates (Anderson, D. C., et al., *Fed. Proc.* 44:2671–2677 (1985); Anderson, D. C., et al., *J. Infect. Dis.* 152:668–689 (1985)). The characteristics of LAD demonstrate that the absence of a functional LFA-1 adhesion molecule causes LAD leukocytes to be substantially incapable of adhering to endothelial cells in a normal fashion. Leukocytes from LAD individuals are unresponsive to those stimuli which induce leukocytes to adhere to and move across vascular endothelial cells (Smith, C. W. et al., *J. Clin. Invest.* 82:1746 (1988)).

The CD11/CD18 complex is also involved in other cell-cell interactions involved in host defense against infection, including binding and phagocytosis of iC3b-opsonized particles, a property of CD11b/CD18 on granulocytes and monocytoid cells, and $Mg^{2+}$-dependent adhesion and killing of target cells by T cells and NK cells, a property of the CD11a/CD18 heteroduplex (Ruoslahti, E. et al., *Science* 238:491 (1987); Anderson, D. C. et al., *Ann. Rev. Med.* 38:175 (1987)).

B. The Adhesion Molecules Of The Super-Immunoglobulin Family

The natural binding ligand for the CD11/CD18 receptor molecules is Intercellular Adhesion Molecule-1 ("ICAM-1" or CD54) (Rothlein R. et al., *J. Immunol.* 137:1270 (1986)), European Patent Application Publication No. 289,949, Simmons, D. et al., *Nature* 331:624–627 (1988); Staunton, D. E. et al., *Cell* 52:925–933 (1988); which references are incorporated herein by reference).

ICAM-1 is a member of the super-immunoglobulin family of molecules. Members of this superfamily are characterized by the presence of one or more Ig homology regions, each consisting of a disulfide-bridged loop that has a number of anti-parallel β-pleated strands arranged in two sheets. Three types of homology regions have been defined, each with a typical length and having a consensus sequence of amino acid residues located between the cysteines of the disulfide bond. (Williams, A. F. et al., *Ann. Rev. Immunol.* 6:381–405 (1988); Hunkapillar, T. et al., *Adv. Immunol.* 44:1–63 (1989)).

ICAM-1 is a cell surface glycoprotein of 97–114 kd. ICAM-1 has 5 Ig-like domains. Its structure is closely related to those of the neural cell adhesion molecule (NCAM) and the myelin-associated glycoprotein (MAG) (Simmons, D. et al., *Nature* 331:624–627 (1988); Staunton, D. E. et al., *Cell* 52:925–933 (1988); Staunton, D. E. et al., *Cell* 61243–254 (1990), herein incorporated by reference).

ICAM-1 is inducible on fibroblasts and endothelial cells in vitro by inflammatory mediators such as IL-1, gamma interferon and tumor necrosis factor in a time frame consistent with the infiltration of lymphocytes into inflammatory lesions in vivo (Dustin, M. L., et. al., *J. Immunol* 137:245–254, (1986); Pober, J. S., et. al., *J. Immunol* 137:1893–1896, (1986)). ICAM-1 is expressed on non-hematopoietic cells such as vascular endothelial cells, thymic epithelial cells, other epithelial cells, and fibroblasts and on hematopoietic cells such as tissue macrophages, mitogen-stimulated T lymphocyte blasts, and germinal center B-cells and dendritic cells in tonsils, lymph nodes and Peyer's patches (Dustin, M. L., et. al., *J. Immunol* 137:245–254, (1986)). ICAM-1 is expressed on keratinocytes in benign inflammatory lesions such as allergic eczema, lichen planus, exanthema, urticaria and bullous diseases.

Thus, ICAM-1 is preferentially expressed at sites of inflammation, and is not generally expressed by quiescent cells. It functions as the cellular substrate to which lymphocytes can attach, so that the lymphocytes may migrate to sites of infection or inflammation.

A "soluble" (i.e., "non-immobilized") fragment of ICAM-1 can be detected in the circulation (Rothlein, R., *J. Immunol.* 147:3788–3793 (1991)). The level of this fragment increases in response to inflammation, suggesting that its level may be a useful diagnostic measure of inflammation (Gearing, A. J. H. et al., *Immunol. Today* 14:506–512 (1993); Rothlein, R., *J. Immunol.* 147:3788–3793 (1991); Blann, A. D. et al., *Thromb Haemost.* 72:151–154 (1994); Cush, J. J. et al., *Arthritis Rheum.* 36:1098–1102 (1993)).

In addition to its role in cellular adhesion, ICAM-1 has been found to be the cellular receptor to which the human rhinovirus binds in order to initiate rhinoviral infection. (Greve, J. M. et al., *Cell* 56:839–847 (1989); Staunton, D. E. et al., *Cell* 56:849–853 (1989); Ohlin, A. et al., *Antimicrob. Agents Chemother.* 38:1413–1415 (1994); Cassanovas, J. M. et al., *J. Virol.* 68:5882–5889 (1994)).

ICAM-2 is a second LFA-1 ligand, distinct from ICAM-1 (Rothlein, R. et al., *J. Immunol.* 137:1270–1274 (1986); Makgoba, M. W. et al., *Eur. J. Immunol.* 18:637–640 (1988); Dustin, M. L. et al., *J. Cell. Biol.* 107:321–331 (1988); Staunton, D. M. et al., *FASEB J.* 3:a446 (1989)). Like ICAM-1, ICAM-2 is a member of the super-immunoglobulin family.

ICAM-2 is constitutively expressed on endothelial cells, and on certain interstitial cells. It is also present on a variety of T- and B-lymphoblastoid cell lines. ICAM-2 is the predominant LFA-1 ligand on unactivated endothelium. It has thus been reported to play a role in normal lymphocyte recirculation, and memory cell recruitment, and to have a role in the interaction of antigen-presenting cells (de Fougerolles, A. R. et al., *J. Exper. Med.* 174:253–267 (1991)).

Recently, ICAM-3, a third LFA-1 ligand was identified (de Fougerolles, A. R. *J. Exper. Med.* 174:253–267 (1991); de Fougerolles, A. R. *J. Exper. Med.* 175:185 (1994); de Fougerolles, A. R. *J. Exper. Med.* 179:619–629 (1994)). ICAM-3 is a heavily glycosylated protein of 124 kD that is expressed on leukocytes but absent from endothelial cells. ICAM-3 shares 53% homology with ICAM-1. ICAM-3 and ICAM-1 appear to be reciprocally expressed: ICAM-3 is expressed by resting cells, and its level falls as a result of cellular activation (Cordell, J. L. et al., *J. Clin. Pathol.* 47:143–147 (1994); El-Gabalawy, H. et al., *Arthritis Rheum.* 37:846–854 (1994)).

C. Other Adhesion Molecules

The selectin (or LECCAM) family of adhesion molecules is a third distinct class of adhesion molecules. Selectins recognize and bind carbohydrate lectins. Three selectins have been described: L-selectin (also termed LECCAM-1, MEL-14, LAM-1, LECAM-1 or lymphocyte homing receptor); E-selectin (also known as endothelial leukocyte adhesion molecule-1 (ELAM-1"), or LECCAM-2); and P-selectin (also known as CD62, platelet activation dependent granule external membrane (PADGEM), LECCAM-3, or granule membrane protein-140 (GMP-140)).

L-selectin is expressed by leukocytes, and plays a role in the "homing" of leukocytes to peripheral lymph nodes (Gallatin, M. W. et al., *Nature* 304:30–34 (1989); Lasky, L. A. et al., *Cell* 56:1045–1055 (1989); Siegelman, M. H. et al., *Proc. Natl. Acad. Sci. (U.S.A.)* 86:5562–5566 (1989); Tedder, T. F. et al., *J. Exper. Med.* 170:123–133 (1989)). It is also expressed on granulocytes.

E-selectin is expressed on endothelial cells in response to cellular stimulation by cytokines such as TNF-$\alpha$ or IL-1$\beta$, or by bacterial endotoxin (LPS) (Bevilacqua, M. P. et al., *Science* 243:1160–1165 (1989); Tedder, T. F. et al., *J. Exper. Med.* 170:123–133 (1989); Bevilacqua, M. P. et al., *Proc. Natl. Acad. Sci. (U.S.A.)* 84:9238–9242 (1987); Luscinskas, F. W. et al., *J. Immunol.* 143:3318–3324 (1989)). In vitro, E-selectin mediates the adhesion of neutrophils, monocytes, eosinophils, a subset of lymphocytes, and certain carcinoma cells. The binding ligand of E-selectin is SLE$^x$ (Lowe, J. B. et al., *Cell* 63:475–484 (1990)). E-selectin is expressed in chronic inflammatory disease such as rheumatoid arthritis.

P-selectin is expressed on platelets and on endothelial cells, neutrophils, other myeloid cells, and a subset of T lymphocytes (Siegelman, M. H., *Curr. Biol.* 1:125–128 (1991); Pober, J. S. et al., *Lab. Invest.* 64:301–305 (1991)). P-selectin and E-selectin bind to a similar spectrum of cells in accordance with the fact that both can bind the SLE$^x$ lectin. The expression of P-selectin is induced by activators such as thrombin, histamine, and hydrogen peroxide.

The expression of E-selectin and P-selectin is reported to reflect inflammatory and hemostatic responses, respectively, to tissue injury (Geng, J. G. et al., *Nature* 343:757–760 (1990); Toothill, V. J. et al., *J. Immunol.* 145:283–291 (1990)). L-selectin has been reported to participate in the recruitment of cells to sites of inflammation (Watson, S. R. et al., *Nature* 349:164–167 (1991); Lewinsohn, D. M. et al., *J. Immunol.* 138:4313–4321 (1987)). All three selectins have been reported to be involved in the recruitment of neutrophils and other leukocytes to sites of inflammation (Arfors, D. E. et al., *Blood* 69:338–340 (1987); Smith, C. W. et al., *J. Clin. Invest.* 82:1746–1756 (1988); Anderson, D. C. et al., *Ann. Rev. Med.* 38:175–194 (1990); Larson, R. S. et al., *Immunol. Rev.* 114:181–217 (1990)).

The selectins have been reported to act by aiding the initial adhesion or "rolling" of neutrophils on activated endothelium (von Andrian, U. H. et al., *Proc. Natl. Acad. Sci. (U.S.A.)* 88:7538–7542 (1991); Ley, K. et al., *Blood* 77:2553–2555 (1991); Lawrence, M. B. et al., *Cell* 65:859–873 (1991); Smith, C. W. et al., *J. Clin. Invest.* 83:2008–2017 (1989)). In contrast, molecules of the CD11/CD18 family are thought to mediate the subsequent arrest of the migrating neutrophils, once they have reached a site of inflammation (Anderson, D. C. et al., *Ann. Rev. Med.* 38:175–194 (1990); Larson, R. S. et al., *Immunol. Rev.* 114:181–217 (1990); Smith, C. W. et al, *J. Clin. Invest.* 83:2008–2017 (1989); Luscinskas, F. W. et al., *J. Immunol.* 146:1617–1625 (1989)).

VCAM-1 (vascular cell adhesion molecule-1) is a cell surface receptor found on vascular cells (Hynes, R. O. *Cell* 48:549–554 (987); Price, G. E., *Science* 246:1303–1306 (1980)). Under normal physiologic conditions, VCAM-1 is either not expressed, or is minimally expressed. It is, however, rapidly induced upon stimulation with TNF-α or IL-1β. VCAM-1 has been shown to bind to the VLA-4 integrin molecule that is expressed on leukocytes and other cells (Springer, T. A., *Nature* 346:425–434 (1990); Hemler, M. E. et al., *ImmunoL Rev.* 114:45–65 (1990)). VLA-4 has been shown to mediate lymphocyte binding to endothelium of mucosal lymph nodes (Holtzmann, B. et al., *Cell* 56:37–46 (1989); (Holtzmann, B. et al. *EMBO J.* 8:1735–1741 (1989)), and to mediate cytotoxic T-cell activity (Hemler, M. E. et al., *J. Biol. Chem.* 262:11478–11485 (1987); Hemler, M. E. et al., In: *Leukocyte Adhesion Molecules* (Springer, T. A. et al., eds.) pp. 44–57, Springer-Verlag, New York (1989)). The expression of VLA-4 is substantially unaffected by cytokines.

Thus, in summary, the ability of leukocytes to maintain the health and viability of an animal requires that they be capable of adhering to other cells (such as endothelial cells). This adherence has been found to require cell-cell contacts which involve specific receptor molecules present on the cell surface of the leukocytes and endothelium. These receptors enable a leukocyte to adhere to other leukocytes or to endothelial, and other non-vascular cells. Humans whose leukocytes lack these cell surface receptor molecules exhibit chronic and recurring infections, as well as other clinical symptoms including defective antibody responses.

Although the process of cellular adhesion can protect humans and other mammals from death due to infection or tissue damage, such protection can come at the cost of significant tissue destruction, inflammation and pain (Horgan, M. J. et al., *Amer. J. Physiol.* 261:H1578–H1584 (1991); Clark, W. M. et al., *J. Neurosurg.* 75:623–627 (1991)). The availability of antibiotics and other modern medical treatments provides alternative approaches to the management of infection and trauma. Thus in many instances, it is desirable to intervene and prevent cellular adhesion from occurring.

Two approaches for accomplishing such intervention have involved the use of anti-CD18 antibodies and anti-ICAM-1 antibodies. Despite promising results in animal models and in vitro tests, the use of such murine monoclonal antibodies has been limited by problems of severe immunoreactivity which lead to the production of anti-murine antibodies.

In view of the desirability of providing a long-term therapy for inflammatory conditions such as asthma, ischemia, graft rejection, transplantation, arthritis, etc., it would be desirable to develop an anti-ICAM-1 antibody that would be significantly less immunogenic than the antibodies previously used. The present invention provides such an improved antibody, as well as methods for its synthesis, purification and use.

BRIEF DESCRIPTION OF THE FIGURES

FIG. 5 shows the immunogenicity of poly(ethylene) glycol-modified enlimomab and native antibody at 28 and 56 days post intravenous injection.

SUMMARY OF THE INVENTION

Figure 1:
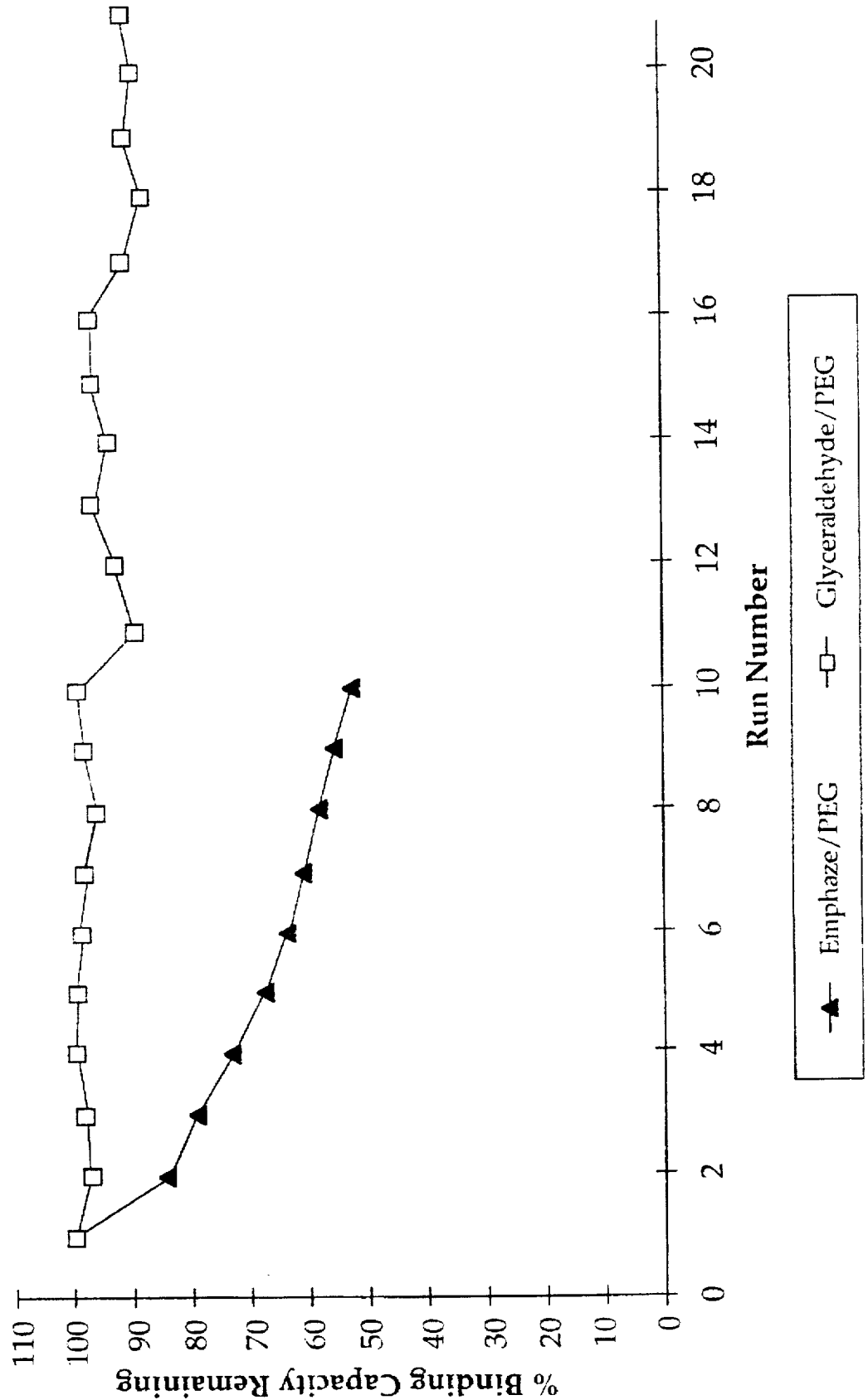
FIG. 1 shows the percentage of binding capacity remaining on an immobilized sICAM-1 column as a function of the number of poly(ethylene) glycol modification runs.

The invention relates to the production and use of modified antibodies that specifically bind to Intercellular Adhesion Molecule-1 ("ICAM-1") in the treatment of inflammation. More specifically, the invention concerns modified non-human anti-ICAM-1 antibodies that, as a consequence of such modification, exhibit improved therapeutic characteristics.

In detail, the invention provides a poly(ethylene) glycol-modified derivative of an anti-ICAM-1 antibody, wherein the antibody is capable of binding to ICAM-1, and of inhibiting ICAM-1-mediated cellular adhesion.

The invention particularly concerns such a poly(ethylene) glycol-modified derivative of the anti-ICAM-1 antibody, wherein the antibody is a monoclonal antibody. The invention particularly concerns the embodiments wherein such derivatives contain an average of from 2 to 15 molecules of a monofunctional poly(ethylene) glycol, and wherein the monofunctional poly(ethylene) glycol is an N-hydroxysuccinimidyl active ester of the propionic acid of poly(ethylene) glycol, an N-hydroxysuccinimidyl active ester of the succcinate poly(ethylene) glycol, an N-hydroxysuccinimidyl active ester of carboxymethylated poly(ethylene) glycol, an N-hydroxysuccinimidyl active ester of the poly(ethylene) glycol dimer with lysine, poly(ethylene) glycol propionaldehyde, or an N-hydroxysuccinimidyl derivative of norleucine poly(ethylene) glycol.

The invention particularly concerns the embodiments wherein the anti-ICAM-1 antibody is (A) antibody enlimomab or (B) an antibody that binds ICAM-1 and that competitively inhibits the binding of enlimomab to ICAM-1, and particularly wherein the derivative retains at least about 20% of the ability of a native anti-ICAM-1 antibody to bind ICAM-1 and/or has an in vivo serum half life that is greater than that of the non-poly(ethylene)glycol modified form of the antibody. BIRR10 is the most preferred poly(ethylene) glycol-modified anti-ICAM-1antibody.

The invention also provides a poly(ethylene) glycol-modified derivative of the anti-ICAM-1 antibody, wherein the derivative is produced by a process comprising:

(a) incubating an anti-ICAM-1 antibody in the presence of an activated poly(ethylene) glycol molecule under conditions sufficient to permit the formation of the poly(ethylene) glycol-modified derivative of the antibody;

(b) subjecting the formed derivative to hydrophobic interaction chromatography under conditions sufficient to permit the separation of poly(ethylene) glycol modified antibody from non-poly(ethylene) glycol modified antibody; and (c) recovering the formed poly(ethylene) glycol modified antibody derivative from the hydrophobic interaction chromatography.

The invention further provides a pharmaceutical composition that comprises:

(a) a poly(ethylene) glycol-modified derivative of an anti-ICAM-1 antibody, wherein the antibody is capable of binding to ICAM-1, and of inhibiting ICAM-1-mediated cellular adhesion; and (b) a physiologically acceptable carrier, excipient, or stabilizer.

It particularly provides such a pharmaceutical composition in which the derivative contains an average of 2 to 15 molecules of a monofunctional poly(ethylene) glycol.

The invention also provides the embodiment wherein the composition contains more than one species of a poly (ethylene) glycol-modified derivative of the antibody, and wherein the species may differ in their respective in vivo serum half lives, as well as the embodiment wherein the composition contains a single species of a poly(ethylene) glycol-modified derivative of the antibody.

The invention provides such pharmaceutical compositions, wherein the poly(ethylene) glycol-modified derivative of the anti-ICAM-1 antibody retains at least about 20% of the ability of a native anti-ICAM-1 antibody to bind ICAM-1 (as measured by, for example, an assay that measures the extent of any competition between such poly (ethylene) glycol-modified derivative and an unmodified antibody for binding to ICAM-1 expressed on JY cells B-lymphoblastoid cells) and/or wherein the poly(ethylene) glycol-modified derivative of the anti-ICAM-1 antibody has an in vivo serum half life that is greater than that of the non-poly(ethylene) glycol-modified form of the antibody.

The invention also provides methods of treating or preventing rhinoviral infection or inflammation (caused by a reaction of either the specific or the non-specific defense system) which comprises providing an effective amount of the above-described pharmaceutical composition to a recipient in need of such treatment or prevention. The compositions and methods of the invention may be used to treat or prevent inflammation associated with autoimmune disease; asthma; adult respiratory distress syndrome; multiple organ injury syndromes secondary to septicemia or trauma; reperfusion injury; acute glomerulonephritis; reactive arthritis; dermatoses with acute inflammatory components; acute purulent meningitis; central nervous system inflammatory disorders; thermal injury; hemodialysis; leukapheresis; ulcerative colitis; Crohn's disease; necrotizing enterocolitis; granulocyte transfusion associated syndromes; or cytokine-induced toxicity.

A method of purifying a poly(ethylene) glycol-modified antibody species from a preparation containing the species and a non-modified species of the antibody, which comprises subjecting the preparation to hydrophobic interaction chromatography under conditions sufficient to separate the non-modified species of the antibody from the poly(ethylene) glycol-modified species, and recovering the separated poly (ethylene) glycol-modified antibody

DESCRIPTION OF THE PREFERRED EMBODIMENTS

1. Anti-ICAM-1 Antibodies

As indicated above, anti-CD18 antibodies and anti-ICAM-1 antibodies have been used to intervene in the cellular adhesion process In vivo studies using anti-CD18 antibodies have shown a reduction in ischemic injury and decreased lung infiltration in heart, lung, intestinal, and systemic shock models (Arfors, K. et al., *Blood* 69:338–340 (1987); Hernandez, L. et al., *Amer. J. Physiol.* 253:H699–H703 (1987); Price, T. et al., *J. Immunol.* 139:4174–4177 (1987); Simpson, P. et al., *J. Clin. Invest.* 81:624–629 (1988); Vedder, N. et al., *J. Clin. Invest.* 81:9393–944 (1988)). Wang, J. H. et al. (*FASEB J.* 8:A981 (1994)) reported that the administration of anti-CD18 and anti-ICAM-1 antibodies to mice had an immunomodulatory effect. The administration of these antibodies has been reported to inhibit ethanol-induced mucosal injury (Dinda, P. K. et al., *Gastroenterol.* 106:A230 (1994)), the onset of autoimmune diabetes (Herold, K. C. et al., *Clin. Res.* 42:119A (1994)), and to prolong the survival of human pancreatic islet xenografts (Zeng, Y. et al., *Transplant. Proceed.* 26:1120 (1994)). Huang, Y. W. et al. (*Hybridoma* 12:661–675 (1993) discuss the use of anti-ICAM-1 antibodies to kill myeloma tumor cell lines.

The capacity of anti-ICAM-1 antibodies to inhibit or prevent tissue damage has been studied in a number of animal modes. Horgan, M. J. et al. (*Amer. J. Physiol.* 261:H1578–H1584 (1991)) reported that a murine monoclonal antibody (RR1/1) directed against ICAM-1 could, in an animal model, prevent the sequestration of neutrophils in the lungs of rabbits that had experienced pulmonary artery occlusion and reperfusion. From studies of a model of central nervous system ischemia (Clark, W. M. et al. (*J. Neurosurg.* 75:623–627 (1991)) reported that the induction of ICAM-1 in central nervous system tissue increases the extent of injury. Archelos, J. J. et al. (*Brain* 116:1043–1058 (1993)) reported that the administration of anti-ICAM-1 antibodies could suppress allergic neuritis in an experimental model.

The administration of anti-ICAM-1 murine monoclonal antibodies has been reported to transiently reduce the extent of ischemic injury in a rabbit model (Clark, W. M. et al., *J. Neurosurg.* 75:623–627 (1991)). Wegner, C. D. et al. (*Lung* 170:267–279 (1992)) confirmed the contribution of leukocyte adhesion and infiltration in the pathogenesis of pulmonary oxygen toxicity in a mouse model, and reported that the administration of a rat anti-ICAM-1 antibody reduced hyperoxic lung injury.

Ma, X. L. et al. (*Circulat.* 86:937–946 (1992)) reported the ability of the anti-ICAM-1 antibody, RR1/1, to inhibit polymorphonuclear leukocyte adherence and infiltration of ischemic myocardial tissue in a feline model. The inhibition significantly protected the feline myocardium from reperfusion-induced injury.

Gorczynski, R. M. et al. (*J. Immunol.* 152:2011–2019 (1994)), used a mouse model to demonstrate that the administration of anti-ICAM-1 antibodies prolonged skin allograft survival after antigen-specific pretransplant immunization or transfusion. Williams, W. W. et al., (*Amer. Soc. Nephrol.* 5:738 (1993) reported the ability of anti-ICAM-1 antibodies to protect the kidney against ischemia. Uchio, E. et al. (*Invest. Ophthalmol. Vis. Sci.* 35:2626–2631 (1994)) reported the ability of anti-ICAM-1 antibodies to prevent experimental uveitis. Zhang, R. L. et a. (*Stroke* 25:266 (1994)) reported that the administration of anti-ICAM-1 reduced ischemic damage in a rat model. Bowes, M. P. et al. (*Exper. Neurol.* 119:215–219 (1993)) reported that the administration of anti-ICAM-1 antibody could reduce the neurological damages associated with stroke in a rabbit cerebral embolism stroke model. Pavilack, M. A. et al. (*Invest. Ophthalmol. Vis. Sci.* 35:1896 (1994)) and Yamigami, S. (*Invest. Ophthalmol. Vis. Sci.* 35:1877 (1994)) reported that the administration of anti-ICAM-1 antibodies improved the viability of corneal grafts.

Such uses of anti-ICAM-1 antibodies, and those described above suggested that cellular adhesion was responsible for exacerbating the tissue damage in inflammatory processes, and that, in model systems, such inflammatory processes could be inhibited. Such studies prompted clinical trials to determine the capacity of anti-ICAM-1 antibodies to provide actual therapeutic benefit.

Haug, C. E. et al., *Transplant.* 55:766–773 (1993) reported the administration of the murine Anti-ICAM-1 antibody, R6.5 (hereinafter designated "enlimomab"), to cynomolgus monkeys who had received renal allografts, and who were risk for delayed graft function. The study established the clinical safety of enlimomab administration. No significant "first-dose" effects were found to be associated with the enlimomab administration, and no adverse systemic effects were detected.

Unfortunately, the antibody was found to be highly immunogenic; almost 90% of recipient animals developed anti-enlimomab antibodies. Indeed, the degree of immunoreactivity was significantly higher than is observed with other murine antibodies. The anti-murine antibody response resulted in the removal ("clearing") of the antibody from the monkeys' sera four days after its administration.

Kavanaugh, A. F. et al. (*Arthritis Rheum.* 35:S43 (1992); *Arthritis Rheum.* 35:S106 (1992); *Clin. Res.* 42:314A (1994); *Immunol.* 91:227 (1993); *Arthritis Rheum.* 36:S40 (1993)) and Schultze-Koops, H. et al. (*FASEB J.* 8:A745 (1994)) reported that the administration of anti-ICAM-1 antibody enlimomab to individuals suffering from rheumatoid arthritis resulted in a rapid clinical improvement. Adverse side-effects of varying severity were noted in most of the patients. The study confirmed the findings of Haug, C. E. et al. that recipients of enlimomab experienced clinically significant relief, but that they mounted a substantial anti-enlimomab response. The pharmacokinetics of the murine anti-ICAM-1 antibody enlimomab is reported by Norris, S. H. et al. (*Pharmaceut. Res.* 10:S334 (1993)).

Omura, T. et al. (*Immunobiol.* 186241–245 (1992)) disclose the rapid rejection of allografted rat livers that had been infused with mouse anti-rat ICAM-1 monoclonal antibodies, and suggested that a circulatory deterioration of the antibody may occur in some instances.

In sum, experiments have demonstrated the in vitro efficacy of anti-ICAM-1 antibodies in preventing or attenuating inflammatory processes. When administered therapeutically, the antibodies have shown an ability to reach their target cells, to cause minimal side effects, and to mediate a significant therapeutic benefit. The therapeutic benefit of anti-ICAM-1 murine antibody administration is, however, associated with a substantial anti-murine immune response. This response has limited the application of anti-ICAM-1 monoclonal antibodies in the treatment of chronic inflammation, and in the treatment of subsequent acute inflammatory disorders.

II. The Modified Antibodies of the Present Invention

The present invention derives in part from the recognition that a modified anti-human ICAM-1 antibody exhibits improved (i.e., decreased) immunoreactivity, while retaining its capacity to inhibit endothelial cell-leukocyte adhesion. The antibody derivative can thus be used to treat or prevent chronic inflammation, or subsequent episodes of acute inflammatory disorders. As used herein, the term "immunoreactivity" is intended to encompass the capacity of an antigen to elicit antibody formation (i.e., immunogenicity) as well as the capacity of an antigen to be recognized by, and become bound to, an antibody.

As used herein, a preparation anti-ICAM-1 antibody, may be for either a "prophylactic" or "therapeutic" purpose. When provided prophylactically, the immunosuppressive compound(s) are provided in advance of any inflammatory response or symptom (for example, prior to, at, or shortly after) the time of an organ or tissue transplant but in advance of any symptoms of organ rejection). The prophylactic administration of the compound(s) serves to prevent or attenuate any subsequent inflammatory response (such as, for example, rejection of a transplanted organ or tissue, etc.). When provided therapeutically, the immuno-suppressive compound(s) is provided at (or shortly after) the onset of a symptom of actual inflammation (such as, for example, organ or tissue rejection, etc.). The therapeutic administration of the compound(s) serves to treat an actual symptom of a present inflammatory response (such as, for example, asthma, arthritis, or the rejection of a transplanted organ or tissue).

The anti-ICAM-1 antibodies that are modified in accordance with the methods of the present invention may be either polyclonal, monoclonal, recombinant or chimeric. Such antibodies may be intact immunoglobulins, or may comprise, for example, fragments (e.g., Fab, F(ab)$_2$, etc.) or sections of intact antibodies.

Murine monoclonal antibodies are particularly preferred. Examples of suitable monoclonal antibodies include RR1/1 (Rothlein, R. et al., *J. Immunol.* 137:1270–1274 (1986)), R6.5 (see, Example 14, below; Rothlein, R., et al., *J. Immunol.* 141:1665–1669 (1988), herein incorporated by reference), LB-2 (Clark, E. A. et al., In: Leukocyte Typing I (A. Bernard, et al., Eds.), Springer-Verlag pp 339–346 (1984)), or CL203 (Staunton, D. E. et al., *Cell* 56:849–853 (1989)). Antibody R6.5, now renamed as "enlimomab" is the most preferred antibody for use in the methods of the present invention. Hybridoma cells that produce antibody R6.5 were deposited with the American Type Culture Collection 12301 Parklawn Drive, Rockville, Md. 20852 on Oct. 30, 1987, and accorded accession number HB-9580.

If desired, additional anti-ICAM-1 antibodies can be obtained using BALB/c mice or equivalent strains. The animals are preferably immunized with approximately 25 µg of human ICAM-1 (or a fragment thereof) that has been emulsified a suitable adjuvant (e.g., Freund's adjuvant, TiterMax adjuvant (Vaxcel, Norcross, Ga.), etc.). Immunization may be conducted at two intramuscular sites, one intraperitoneal site, and one subcutaneous site at the base of the tail. An additional intravenous (IV) injection of approximately 25 µg of ICAM-1 is preferably given in normal saline three weeks later. After approximately 11 days following the second injection, the mice may be bled and the blood screened for the presence of anti-ICAM-1 antibodies. Preferably, an ELISA is employed for this purpose. A suitable assay is described by Norris, S. H. et al. (*J. Pharm. Biomed. Anal.* 9:211–218 (1991), herein incorporated by reference). The principle of the assay involves the measurement of any competition between a novel antibody and biotinylated enlimomab for binding to ICAM-1 expressed on JY B-lymphoblastoid cells that have been bound to a microtiter plate.

Most preferably, the mouse having the highest antibody titer is given a third IV injection of approximately 25 µg of ICAM-1. The splenic leukocytes from this animal may be recovered 3 days later, and are then permitted to fuse, most preferably, using poly(ethylene) glycol, with cells of a suitable myeloma cell line (such as, for example, the P3X63Ag8.653 myeloma cell line). Hybridoma cells are selected by culturing the cells under "HAT" (hypoxanthine-aminopterin-thymine) selection for about one week. The resulting clones may then be screened for their capacity to produce monoclonal antibodies ("mAbs") to ICAM-1, preferably by ELISA.

In a preferred procedure for obtaining monoclonal antibodies, the spleens of the above-described immunized mice are removed, disrupted and immune splenocytes are isolated over a ficoll gradient. The isolated splenocytes are fused, using poly(ethylene) glycol with BALB/c-derived HGPRT (hypoxanthine guanine phosphoribosyl transferase) deficient P3x63xAg8.653 plasma-cytoma cells. The fused cells are plated into 96 well microtiter plates and screened for hybridoma fusion cells by their capacity to grow in culture medium supplemented with hypothanthine, aminopterin and thymidine for approximately 2–3 weeks. On average, out of every $10^6$ spleen cells subjected to fusion yields a viable hybridoma. A typical spleen yields $5$–$10 \times 10^7$ spleen cells.

Hybridoma cells that arise from such incubation are preferably screened for their capacity to produce an immunoglobulin that binds to ICAM-1. An indirect ELISA may be used for this purpose. In brief, the supernatants of hybridomas are incubated in microtiter wells that contain immobilized ICAM-1. After washing, the titer of bound immunoglobulin is determined using, for example, a goat anti-mouse antibody conjugated to horseradish peroxidase. After additional washing, the amount of immobilized enzyme is determined (for example through the use of a chromogenic substrate). Such screening is performed as quickly as possible after the identification of the hybridoma in order to ensure that a desired clone is not overgrown by non-secreting neighbors. Desirably, the fusion plates are screened several times since the rates of hybridoma growth vary.

As indicated, antibody enlimomab is the most preferred anti-ICAM-1 antibody of the present invention. Enlimomab is a murine IgG2a monoclonal antibody (mAb). Upon administration to rabbits, the antibody has a serum elimination half-life of 24–29 hours (Norris, S. H. et al., *J. Pharm. Biomed. Anal.* 9:211–218 (1991)). Phase I human clinical trials involving the "add on" administration of enlimomab to recipients of renal or lung transplants revealed that, in humans, enlimomab has a serum elimination half-life of between 5.8 and 39.1 hours (Norris, S. H. et al., *Pharmaceut. Res.* 10:S334 (1993)).

One aspect of the present invention concerns the determination that by modifying such anti-ICAM-1 it is possible to substantially decrease the immunoreactivity of the antibody and thus increase its serum elimination half-life while retaining the in vivo therapeutic efficacy of the antibody. Preferred modifications include modifying the antibody to contain poly(ethylene) glycol ("PEG") adducts. PEG is mildly hydrophobic material having very high aqueous solubility.

A further aspect of the present invention concerns the ability to purify and obtain homogeneous species of poly (ethylene) glycol-modified antibodies having defined and uniform degrees of poly(ethylene) glycol-modification.

Most preferably, the poly(ethylene) glycol-modification reaction is conducted using "activated" PEG derivatives. As used herein, "activated PEG derivatives" are derivatives of PEG bearing electrophilic groups that are reactive toward amines (such as lysines) and other nucleophiles are referred to as "activated PEGs."

These PEGs have been used extensively for attachment of PEG to proteins and in liposome formulations (Davis, F. F. et al., U.S. Pat. No. 4,179,337; Rhee, W. et. al., U.S. Pat. No. 5,304,595; Delgado, C. et. al., U.S. Pat. No. 5,349,052; Garman, A. J., U.S. Pat. No. 4,935,465; Braatz, J. A. et al., U.S. Pat. No. 5,091,176; Harris, J. M. et al., U.S. Pat. No. 5,252,714; Woodle, M. C. et al., U.S. Pat. No. 5,356,633; Nucci, M. L. et al., *Adv. Drug Del. Rev.* 6:133 (1991); Ajisaka, K. et al., *Biochem. Biophys. Res. Commun.* 97:1076 (1980); Boccu, E. et al. *Pharmacol. Res. Commum.* 14:113 (1982); Beauchamp, C. O. et al., *Anal. Biochem.* 131:25 (1983); Rajagopalan, S. et al., *J. Clin. Invest.* 75:413 (1985); Knauf, M. J. et al., *J. Biol. Chem.* 263:15064 (1988); Abuchowski, A. et al., *J. Biol. Chem.* 252::3578 (1977); Davis, S. et al., *Lancet* 2:281 (1981); Kamisaki, Y. et al., *J. Pharmacol. Exper. Ther.* 216:410 (1981); Fuertges, F. et al., *J. Contr. Rel.* 11:139 (1990); Ho, D. H. et al., *Drug Metab. Dispos.* 14:349 (1986); Ho, D. H. et al., *Drug Metab. Dispos.* 16:27 (1988); Park, Y. K. et al., *Anticanc. Res.* 1:373 (1981); Abuchowski, A. et al., *Canc. Treat. Rep.* 63:1127 (1979); Abuchowski, A. et al., *Canc. Treat. Rep.* 65:1077 (1981); Bendich, A. et al., *Clin. Exper. Immunol.* 48:273 (1982); Davis, S. et al., *Clin. Exper. Immunol.* 46:649 (1981)).), liposomes (Allen, T. M. et al., *Biophys. Biochem. Acta* 1061:56 (1991); Allen, T. M. et al., *Biophys. Biochem. Acta* 1066:29 (1991); Blume, T. M. et al., *Biophys. Biochem. Acta* 1061:56 (1991); Klibanov, A. L. et al., *Biophys. Biochem. Acta* 1062142 (1992); Senior, J. et al., *Biophys. Biochem. Acta* 106277 (1991)), soluble and insoluble polymers and a variety of poly(ethylene) glycol-modified molecules of biological relevance (commonly described as "poly(ethylene) glycol-modified molecules").

Of particular importance, for the aforementioned applications, are the monofunctional polymers which are capped on one end with a methyl ether group (mPEG). Reactions of activated PEGs are free from crosslinking and can result in attachment of multiple strands of the polymer to the target molecule. Choice of the appropriate derivative for the specific application is best made by considering a variety of properties such as: desired point of attachment (lysine vs. cysteine): hydrolytic stability and reactivity of the derivative; stability, toxicity and antigenicity of the linkage and suitability for analysis.

The N-hydroxysuccinimidyl (or NHS)active esters of PEG succinate (SS-PEG) have been the reagents of choice for attachment of PEG to proteins or peptides in many laboratories. These derivatives react with amino groups on proteins under mild conditions in short periods of time (approximately 30 minutes at 4° C., pH 8.5) and yield extensively modified, yet active, conjugates. The succinimidyl succinate possesses an ester link in its backbone and thus has the property of undergoing relatively rapid hydrolysis in vivo. More stable PEG conjugates can be made by use of the succinimidyl derivative of PEG propionic acid (SPA-PEG), which does not possess the ester linkage. This is also true of the corresponding succinimidyl derivative of carboxymethylated PEG (SCM-PEG) which is even more reactive than the SPA-PEG. SCM-PEG is extremely reactive both toward hydrolysis and aminolysis with an hydrolysis half life of less than one minute at pH 8.0 (however, the extreme reactivity of this derivative provides an advantage in a reaction which proceeds to completion at a high rate making the poly(ethylene) glycol modification highly selective). This has been shown to result in highly poly (ethylene) glycol-modified enzymes which retain nearly 100% specific activity relative to the native protein. Presumably, the PEG derivative lifetime limits its reactivity to lysines at the very surface of the protein where their placement is less likely to disrupt secondary structure leading to a reduction in specific activity.

Activated monomethoxypoly(ethylene) glycol (mPEG) of molecular weight 5 kD is the most preferred agent for modifying the antibodies of the present invention. The mPEG is activated by the presence of an N-hydroxysuccinimidyl ("NHS") moiety. Activated monomethoxypoly(ethylene) glycol (mPEG) of up to molecular weight 40 kD may alternatively be employed. Suitable activated monofunctional poly(ethylene) glycols include N-hydroxysuccinimidyl active esters of the propionic acid of poly(ethylene) glycol ("SPA-PEG"), N-hydroxysuccinimidyl active esters of the succcinate poly (ethylene) glycol ("SS-PEG"), N-hydroxysuccinimidyl active esters of carboxymethylated poly(ethylene) glycol ("SCM-PEG"), N-hydroxysuccinimidyl active esters of the poly(ethylene) glycol dimer with lysine ("PEG2-NHS"), poly(ethylene) glycol propionaldehyde ("PEG-ALDEHYDE"), or N-hydroxysuccinimidyl derivatives of norleucine poly(ethylene) glycol ("PEG-NORLEUCINE").

The most preferred activated mPEG is an N-hydroxysuccinimidyl derivative of mPEG propionic acid ("SPA-PEG"). Polymerization of mPEG monomers results in the production of poly(ethylene) glycol-modified ("poly (ethylene) glycol-modified") antibodies, which are the most preferred modified antibodies of the invention.

Much literature has been devoted to the study of protein modification by attachment of polyethylene glycol (PEG) of various molecular weights ranging from 5K to 40K or higher. As indicated, PEG has been reported attached to enzymes, peptides and proteins.

The use of poly(ethylene) glycol to decrease the immunoreactivity of proteins or antibodies has been described in the art (Davis, F. F. et al., U.S. Pat. No. 4,179,337; Ono, K. et al., U.S. Pat. No. 5,342,940; Tomasi, T. B. et al., U.S. Pat. No. 4,732,863; Katre, N. et al., U.S. Pat. No. 4,917,888; Nakagawa, Y. et al., U.S. Pat. No. 4,791,192; Saifer, M. et al., U.S. Pat. No. 5,283,317; Cunningham-Rundles, C., U.S. Pat. No. 5,169,627).

In a limited number of cases, poly(ethylene)glycol has been used to modify antibodies. Tomasi, T. B. et al. (U.S. Pat. No. 4,732,863) discuss a method for producing poly (ethylene) glycol-modified antibodies, and disclose that such antibodies exhibit reduced immunogenicity. The method involves the covalent attachment of PEG to trinitrobenzene sulfonic acid-available amino groups on the protein molecule.

Tomasi, T. B. et al. (U.S. Pat. No. 4,732,863) disclose that the immunogenicity of PEG-modified antibody varies with the degree of modification, and that it is therefore important to control the number of PEG molecules attached to the antibody in order to balance the reduced immunoreactivity of the antibodies with the need to preserve a sufficient degree of antibody activity. Tomasi et al. disclose that immunoglobulins in which 13–18% of the amino groups have been modified generally lack detectable immunogenicity, but that percent modifications outside of this range have an unpredictable effect on immunogenicity. The extent of poly (ethylene) glycolation is said to be controllable by adjusting the ratio of antibody to monomer.

Methods of forming and using poly(ethylene) glycol-modified antibodies are discussed by Karr, L. J. et al. (*Meth. Enzymol.* 228:377–390 (1994)).

These protein modifications are intended to extend the half life of the native molecule and/or reduce or eliminate the inherent immunogenicity of foreign source proteins being used as human therapeutics. Most of the effort reported has been on the procedures used in these modification studies, the synthesis of the PEG derivatives and the end result in animal studies or human clinical trials; however, there remains a shortage of analytical methods which characterize poly(ethylene) glycol modified proteins. Little attention has been given to determining quantitatively the extent of poly(ethylene) glycol modification by chromatographic techniques or determining unmodified protein remaining at the conclusion of the reaction. A few attempts have been made to analyze this heterogeneity and no technique has emerged which is suitable for resolution of a PEG-protein preparation into individual components.

One aspect of the present invention thus concerns a new hydrophobic interaction chromatography method capable of separating not only native monoclonal antibody or Fab fragments from poly(ethylene) glycol-modified versions of these molecules but also allowing the separation of individual modified species varying in the number of attached PEG strands. This method takes advantage of the partitioning of PEG-modified protein into PEG-rich phases which is an effective technique in aqueous polymer two-phase separations. This new chromatographic technique works equally well for proteins modified with 5K PEG derivatives or those modified with PEG of higher molecular weight. The method has been developed both as a quantitative analytical tool as well as a preparative purification step for the removal of unmodified native protein subsequent to poly(ethylene) glycol-modification.

Intercellular adhesion molecule-1 (ICAM-1) is involved in the pathogenesis of many inflammatory conditions. Modulation of cell adhesion through the interference with ICAM-1-dependent interactions has been demonstrated to be beneficial in preclinical models and/or in the clinical treatment of various acute conditions such as burn, graft rejection, ischemia-reperfusion injury (Cosimi, A. B. et al., In: *Structure, Function and Regulation of Molecules Involved in Leukocyte Adhesion,*. Lipsky, P. E., et al. , Eds., Springer Verlag, pp. 373–387 (1992); Mileski, W. J. et al., *J. Surg. Res.* 52:334–339 (1992); Hau, C. E. *Transplantation* 55:766–773 (1993); Lefer, A. M. et al ., *Ann. Rev. Pharmacol. Toxicol.* 33:71–90. 1993)). Furthermore, anti-ICAM-1 antibody therapy has been effective in the treatment of chronic inflammatory disease such as rheumatoid arthritis (Kavanaugh, A. et al. , *Arthr. Rheum.* 35:S43 (1992)). However, in many instances, and especially when the condition being treated is a reoccurrence of a prior-treated inflammatory process, anti-ICAM-1 therapy may not be utilized because of the immune response (which was induced by the initial administration of the antibody) against the antigenic determinants of the foreign murine proteins that comprise the enlimomab molecule. Modification of the antibody structure to reduce immunogenicity is the primary goal of antibody engineering usually attained through "humanization" by molecular biological techniques. However, this approach often leads to alterations of the antibody that compromise antibody function. These protein modifications are intended to extend the half life of the native molecule and/or reduce or eliminate the inherent immunogenicity of foreign source proteins being used as human therapeutics.

III. Methods of Modification

One aspect of the present invention concerns two improved methods for poly(ethylene) glycol modification of antibodies in general, and of anti-ICAM-1 antibodies, in particular. The two methods are referred to as the "solution" method and the "column" method.

Solution-Based Poly(ethylene) Glycol-modification

In the solution method of poly(ethylene) glycol-modification, the anti-ICAM-1 antibody and activated mPEG are stirred in a buffered aqueous solution, and the conjugation reaction is quenched after proceeding to the desired point.

Reactions are quenched by adding diglycine to the reaction mixture to a 50 fold molar excess over the available amino groups on the antibody. Reaction contaminants (e.g., unreacted mPEG, diglycine, etc.) are removed from the reaction mixture by either diafiltration or dialysis, and buffer exchanged into 50 mM sodium phosphate, 100 mM sodium chloride, pH 6. Solutions are then sterile filtered prior to storage at 4° C.

B. Column-Based Poly(ethylene) Glycol-modification

In the column method, the anti-ICAM-1 antibody is first bound to an immobilized ligand which presents an ICAM-1 or an ICAM-1-like epitope. Such binding thus involves that region of the antibody that can bind with ICAM-1. In one embodiment, the immobilized ligand is a soluble form of ICAM-1 ("sICAM-1") that has been covalently attached to a chromatography column resin. Alternatively, an anti-idiotypic antibody of enlimomab (such as the monoclonal antibody CA3) can be used for this purpose (Rothlein, R. et al., Intl. Arch. Allerg. Immunol. 100:121–127 (1993), herein incorporated by reference) It thus binds anti-ICAM-1 antibodies in a manner that is the equivalent of sICAM-1.

In one preferred embodiment for column poly(ethylene) glycol-modification, an sICAM-1 affinity column is first prepared using Emphaze activated chromatography resin (azlactone chemistry). sICAM-1 is preferably diafiltered into a coupling buffer (860 mM $Na_3$Citrate, 100 mM $NaHCO_3$, pH 8.6) and the concentration is adjusted to approximately 10 mg/ml. Emphaze Biosupport Medium is then added to the solution to give 1 ml of swollen resin for each 20 mg of sICAM-1. The resin is mixed into the sICAM-1 solution with vortexing and the suspension is gently agitated for 1 hour at room temperature. Uncoupled sICAM-1 is removed by washing the resin (e.g., for ten times with one equal volume of PBS (50 mM sodium phosphate, 100 mM NaCl), pH 6, in a 25 μm sintered glass fritted tube). Unreacted azlactone groups are quenched by gently mixing the resin twice with ethanolamine (pH 9) (e.g., 1 volume of ethanolamine first for 30 minutes and then for 2 hours). The resin is extensively washed (e.g., for ten times with one volume of 1M NaCl followed by three times with one volume of PBS, pH 6). The resin may then be packed into a chromotographic column, washed with several (e.g., three) column volumes of a suitable storage buffer (such as 64 mM sodium phosphate, 86 mM NaCl, 2% (v/v) glycerol, 0.05% sodium azide, pH 6) and stored at 4° C.

To determine the coupling efficiency of the sICAM-1 to the Emphaze resin, the amount of unbound sICAM-1 from the coupling reaction may be quantitated, preferably using the BCA method. This is accomplished by quantitating unbound sICAM-1 in the resin wash solution; the coupling efficiency is estimated to be >95%. The capacity of the sICAM-1 affinity column is determined by sequentially loading the column until breakthrough of enlimomab is observed. The binding capacity ranges from 8.2 to 8.8 mg enlimomab per ml of gel. This represents a binding mass ratio of 1:2 (enlimomab: sICAM-1), or a molar ratio of one enlimomab to four sICAM-1 molecules. For a scalable process, it is desirable to use a resin that loses very little capacity after each poly(ethylene) glycol-modification run and which with each run produces a consistent poly(ethylene) glycol-modified product.

The conjugation reaction is run with the antibody bound to the sICAM-1 column, thus masking the binding site from PEG attachment. While both the column and solution methods produce mPEG-anti-ICAM-1 antibody conjugates that retain binding activity, the column method permits more mPEG to be attached to the antibody with a greater retention of binding activity. Moreover, the column method permits one to protect the binding site of enlimomab from the poly(ethylene) glycol-modification process, and thereby permits the isolation of a poly(ethylene) glycol-modified antibody derivative that retain greater binding capacity. The column method is thus the preferred method superior for the attachment of mPEG to anti-ICAM-1 antibody. The methods are described below with reference to enlimomab, the preferred anti-ICAM-1 antibody.

The sICAM-1 affinity column is then equilibrated with 5 column volumes of PBS, pH 7.5, and the column is loaded to capacity with enlimomab (2–5 mg/ml in PBS, pH 7.5). A solution of activated SPA-PEG (5 kD) is prepared in one column volume of PBS, pH 7.5. The mPEG solution typically contains one milligram of mPEG for each milligram of enlimomab loaded onto the sICAM-1 column. The mPEG solution is recycled over the sICAM-1 column for one hour at room temperature and then removed by washing the column with five volumes of equilibration buffer. The mPEG-enlimomab molecule produced through the column method (designated "BIRR10") can then be eluted with two column volumes of 100 mM glycine, pH 2.7, and neutralized with 1M Tris-base, pH 9 or 100 mM sodium carbonate (pH 11) and then neutrilized with 1M sodium phosphate (pH 4.5).

The crude mPEG-enlimomab mixture produced by both the solution and column poly(ethylene) glycol-modification processes contains residual (2–5%) unpoly(ethylene) glycol-modified enlimomab. Since this material comprises an immunogenic contaminant, it is desirable to remove it from the preparation. Unpoly(ethylene) glycol-modified enlimomab is preferably removed from mPEG-enlimomab preparations by either preparative size exclusion chromatography or hydrophobic interaction chromatography.

IV. Purification of Poly(ethylene) Glycol-modified Antibody

A. Size Exclusion Chromatography

For size exclusion chromatography a concentrated crude pool of BIRR10 is loaded onto a column containing an appropriate preparative size exclusion chromatography column (such as a 2.6×60 cm column containing Pharmacia Superdex 200) that had been equilibrated in a suitable buffer (e.g., 64 mM sodium phosphate, 86 mM NaCl, pH 6). The single broad peak that emerged is fractionated to remove both ends, the front end containing highly poly(ethylene) glycol-modified enlimomab, and the late tail containing lightly poly(ethylene) glycol-modified and native enlimomab.

B. Hydrophobic Interaction Chromatography

Two main problems were encountered in attempts to develop unique analytical techniques for the characterization of poly(ethylene) glycol-modified protein adducts while resolving the individual components. First, the number of species in a preparation varies depending upon the technique of poly(ethylene) glycol-modification used (i.e. chemistry of PEG derivative, molecular weight, and number of reactive sites on protein). Furthermore, the resolution of the different analytical techniques varies between proteins. Second, although heterogeneity is revealed there is a lack of resolution in individual poly(ethylene) glycol-modified species. Both problems can be resolved utilizing specific HPLC column technology.

PEG is a mildly hydrophobic material with very high aqueous solubility. It has been used to modify proteins, thereby increasing their serum half lives, and has been utilized in aqueous 2-phase partitioning systems. This unique polymer possesses many other interesting properties which make it a frequently used component of pharmaceutical formulations and food preparations (Abuchowski, A. et al., Canc. Biochem. Biophys. 7:175–186 (1984); Mast, A. E. et al. (J. Lab. Clin. Med. 116:58–65 (1990); Nakayomi, K. et al., Biochem. Intl. 22:75–84 (1990); Sada, E. et al., J. Ferment. Bioeng. 71:137–139 (1991); Matsuyama, H. et al., Chem. Pharm. Bull. 39:743–746 (1991); Zalipsky, S. et al., Biotechnol. App. Biochem. 15:100–114 (1992))

In the most preferred embodiment, hydrophobic interaction chromatography is employed to remove non-poly (ethylene) glycol-modified antibody, as well as to provide a homogeneous species of antibody having a desired degree of poly(ethylene) glycol-modification.

Hydrophobic interaction chromatography ("HIC") is a valuable technique for the separation of proteins under high salt conditions (see, generally, HPLC of Biological Macromolecules. *Methods and Applications*, Gooding, K. M. et al., Eds., Marcel Dekker, Inc. (1990)). With regard to proteins, HIC separation is based on the interactions of the hydrophobic amino acid residues of the protein with immobilized hydrophobic moieties immobilized to a chromatographic support. The immobilized hydrophobic moieties may be selected from a broad range of alkyl and aryl groups. PEG is a preferred immobilized moiety. The hydrophobicity of the moiety increases with increasing alkyl length. The protein is adsorbed to the column in high salt (1–2M $NH_4(SO_4)_2$ being preferred), and is eluted by lowering the ionic strength. Methods of conducting HIC are described by Cameron, G. W. et al. (*Meth. Molec. Cell. Biol.* 4:184–188 (1993)), Raymond, J. et. al. (*J. Chromatog.* 212:199–209 (1981)), Ochoa, J. I. (*Biochimie* 60:1–15 (1978)), Roggenbuck, D. et al. (*J. Immunol. Meth.* 167:207–218 (1994)), Michaelson, S. et al. (*Pol. J. Food Nutr. Sci.* 3/44:5–44 (1994), Rippel, G. et al. (*J. Chromatog.* 668:301–312 (1994)), Szepesy, L. et al. (*J. Chromatog.* 668:337–344 (1994)), Huddleston, J. G. et al. (*Biotechnol. Bioeng.* 44:626–635 (1994)), Watanabe, E. et al. (*Annl. NY Acad. Sci.* 721:348–364 (1994)), all of which references are herein incorporated by reference.

The attachment of polyethylene glycol strands to a large protein (i.e. a monoclonal antibody has been shown to increase the hydrophobicity of the antibody relative to the native unmodified antibody). In high salt buffer conditions, which eliminate charge effects and maximize hydrophobic effects one should be able to separate native protein from poly(ethylene) glycol modified protein using a hydrophobic ligand. A variety of commercially available HIC column chemistries which span a wide range of hydrophobicities should make it possible to find an appropriate ligand which allows for chromatographic separation. One also might expect an HIC ligand similar in structure to poly(ethylene) glycol to enhance partitioning in a pseudo-affinity mode since poly(ethylene) glycol modified proteins are known to preferentially partition into PEG phases in 2-phase separation systems (Walter, H. et al., In: *Partitioning in Aqueous Two-Phase Systems, Theory, Methods, Uses and Applications to Biotechnology*, Academic Press, New York (1985); Karr, L. J. et al., *J. Chromatogr.* 354:269 (1986); Stocks, S. J. et al., *Anal. Biochem.* 73:86 (1988); Karr, L. J. et al., In: *Separations Using aqueous Phase Systems. Applications in Cell Biology and Biotechnology*, Fisher, D. et al., Eds., Plenum Press, New York (1989)). The same principle of partitioning should apply equally well in chromatographic system as has been demonstrated to work in these two-phase systems. While hydrophobic interactions will predominate, the specific interaction between PEG attached to the protein and the PEG-bonded phase may be strong enough to facilitate chromatographic separation of the native protein from the poly(ethylene) glycol modified protein, in addition to resolving individual PEG-protein adducts.

A variety of commercially available HIC column chemistries which span a wide range of hydrophobicities were evaluated. HIC columns purchased from Synchrom and Bio-Rad covering the full range in available alkyl ligand hydrophobicity from hydroxypropyl to pentyl plus phenyl were initially tested. In most cases a satisfactory separation of native from PEG-modified protein was not achieved.

When highly poly(ethylene) glycol modified samples were chromatographed on certain columns the increased hydrophobicity of the PEG-modified antibody was evident in the increase in retention time relative to native protein. However, these columns failed to separate native protein from poly(ethylene) glycol-modified protein when samples containing both native unmodified antibody and a mixture of poly(ethylene) glycol-modified species were chromatographed. Since the poly(ethylene) glycol-modification procedures used in our studies leave some non-poly(ethylene) glycol-modified antibody (as determined by other techniques, i.e., non-reduced SDS-PAGE) a chromatographic method needed to be developed which was able to separate the two components. This was immunologically important as it has been demonstrated that even small amounts of unmodified native protein contaminating the poly(ethylene) glycol-modified protein may cause an immune response.

Rainin's Hydropore HIC column was tested for its ability to separate native protein from PEG modified protein. This column has the unique property of incorporating PEG as the hydrophobic ligand on a silica based particle (Hatch, R. G., *J. Chromatogr. Sci.* 28:210 (1990); Chang, J. et al., *J. Chromatogr.* 319:396 (1985)). The hypothesis of enhancing the hydrophobic interactions with PEG as a bonded phase was tested using this column. This unique chemistry performed well allowing not only separation of the native antibody from the poly(ethylene) glycol-modified species and quantitation of the remaining unmodified antibody but also provided separation of the individual 1-PEG, 2-PEG, 3-PEG modified species. With only slight modifications this technique was scaled up and used to purify large quantities of native-free poly(ethylene) glycol-modified monoclonal antibody.

Synchropak columns were purchased from Synchrom Inc., Lafayette Inc. and are a series of mildly hydrophobic interaction columns for use with proteins and enzymes. This column is composed of 6.5µ 300 Å macroporous spherical silica covalently bonded with a polyamide coating which is derivatized with a hydrophobic ligand such as propyl, pentyl or hydroxypropyl.

The Bio-Gel TSK phenyl-5-PW column were also tested. The column was purchased from Bio-Rad, Hercules Calif. These particles are comprised of 10.0µ 1000 Å macroporous hydroxylated polyether beads bonded with a very low surface density of the hydrophobic phenyl ligand.

Hydropore columns were also employed. The columns were purchased from Rainin Instrument Co., Emeryville Calif. The packing consists of 300 Å pore size high purity silica, chemically bonded with a proprietary hydrophilic organic layer. Poly(ethylene) glycol groups are then covalently attached to the hydrophilic monolayer to produce a chromatographic material. Poly(ethylene) glycol (PEG) is a weakly hydrophobic neutral polymer. PEG is bonded at a surface density that retains proteins at high salt concentrations through interactions between the bonded phase and hydrophobic areas of the protein surface. Proteins are then released at low salt concentrations with high yield.

An HIC method was developed for use both as an analytical tool and for the preparative separation of unpoly (ethylene) glycol-modified enlimomab from the poly (ethylene) glycol-modified BIRR10. The method takes advantage of the partitioning of the PEG modified protein into PEG rich phases as has been demonstrated in aqueous polymer two-phase separations. Using this chromatographic technique, it is possible to rapidly determine the percentage of native enlimomab in poly(ethylene) glycol-modification preparations. The poly(ethylene) glycol-modified material can then be purified on a larger scale using the same HIC column material. In addition to being able to quantitate native antibody in poly(ethylene) glycol-modified samples this method also provides a fingerprint of the poly(ethylene) glycol-modification reaction and can be utilized in quality control for batch-to-batch variability testing. Since it is possible to determine (using appropriate software) the area of individual peaks by this method, the technique can also be used to monitor stability of poly(ethylene) glycol-modified proteins and the time course of the poly(ethylene) glycol-modification process. This task is accomplished using commercially available HIC column material which are available in a variety of particle sizes.

In accordance with this method, BIRR10 is applied to an HIC column in a suitable salt solution (e.g., 2M $(NH_4)_2SO_4$, 100 mM phosphate, pH 7.0). A step gradient is run with the native enlimomab eluting first as the ammonium sulfate concentration is dropped to 0.9M $(NH_4)_2SO_4$ in 100 mM phosphate, pH 7.0. When the salt concentration is dropped further (0.5M $(NH_4)_2SO_4$ in 100 mM phosphate, pH 7.0), the BIRR10 us eluted from the column as a single peak.

The BIRR10 purity and identity may be measured using a variety of analytical methods including, reduced and non-reducing sodium dodecyl sulfate polyacrylamide gel electrophoresis (SDS-PAGE) size exclusion chromatography, analytical HIC, capillary electrophoresis, laser desorption mass spectrometry and circular dichroism. Densitometric scanning of non-reduced Coomassie-stained SDS-PAGE gels allows estimation of the relative band areas of each poly(ethylene) glycol-modified species. This procedure estimates approximately an average of 5 PEGs per BIRR10 molecule. Laser desorption mass spectrometry further corroborates these data. Analytical size exclusion chromatography further characterizes BIRR10. A Superdex 200 gel filtration column is calibrated with globular protein standards and enlimomab and BIRR10 compared. Enlimomab elutes with an apparent Stokes radius of a 200 kD protein while BIRR10 has an apparent Stokes radius of 540 kD. The addition of five 5 kD PEGs increases the Stokes radius by 2.6 fold.

If the mixture of poly(ethylene) glycol-modified and non-poly(ethylene) glycol-modified material is processed as described above, and analytical hydrophobic interaction chromatography is performed, no native nonpoly(ethylene) glycol-modified material can be detected in the preparation.

V. Administration of Poly(ethylene) Glycol-modified Anti-ICAM-1 Antibody

The antibody molecules of the present invention can be formulated according to known methods to prepare pharmaceutically useful compositions, whereby these materials, or their functional derivatives, having the desired degree of purity are combined in a mixture with a physiologically acceptable carrier, excipient, or stabilizer. Such materials are non-toxic to recipients at the dosages and concentrations employed. A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

The antibodies of the present invention may be prepared and administered in the same manner as has been described for non-ICAM-1 antibodies (Basta, M. et al., U.S. Pat. No. 5,171,663; Landucci et al., U.S. Pat. No. 5,308,626; Doleschel, W. et al., U.S. Pat. No. 4,880,913; Curry, W. M. et al., U.S. Pat. No. 4,719,290; Safai, B. et al., U.S. Pat. No. 4,649,115; Uemura, Y. et al., U.S. Pat. No. 4,692,331; Kimura, T. et al., U.S. Pat. No. 4,379,086; Uemura, Y. et al., U.S. Pat. No. 4,371,520; Osther, K. B., U.S. Pat. No. 5,286,852; all herein incorporated by reference).

Suitable vehicles and their formulation, inclusive of other human proteins, e.g., human serum albumin, are described, for example, in Remington's Pharmaceutical Sciences (16th ed., Osoi, A., Ed., Mack, Easton Pa. (1980)). In order to form a pharmaceutically acceptable composition suitable for storage or administration, such compositions will contain an effective amount of one or more species of poly(ethylene) glycol-modified anti-ICAM-1 antibody.

The compositions of the present invention will preferably be formulated for administration parenterally by injection, rapid infusion, nasopharyngeal absorption (intranasopharangeally), dermoabsorption, or orally. The compositions may alternatively be administered intramuscularly, or intravenously. Compositions for parenteral administration include sterile aqueous or non-aqueous solutions, suspensions, and emulsions. Examples of non-aqueous solvents are propylene glycol, poly(ethylene) glycol, vegetable oils such as olive oil, and injectable organic esters such as ethyl oleate. Carriers, adjuncts or occlusive dressings can be used to increase tissue permeability and enhance antigen absorption. Besides the inert diluents, such compositions can also include wetting agents, emulsifying and suspending agents, or sweetening, flavoring, coloring or perfuming agents.

Optionally other ingredients may be added such as antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinyl pyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; and sugar alcohols such as mannitol or sorbitol.

Generally, the dosage needed to provide an effective amount of the composition will vary depending upon such factors as the recipient's age, condition, sex, and extent of disease, if any, and other variables which can be adjusted by one of ordinary skill in the art. Effective amounts of the compositions of the invention can vary from 0.01–1,000 mg/ml per dose or application, although lesser or greater amounts can be used.

The pharmaceutical compositions used for therapeutic administration may be sterilized, as by filtration through sterile filtration membranes (e.g., 0.2 micron membranes). The compositions may be stored in lyophilized form or as a liquid solution.

The poly(ethylene) glycol-modified anti-ICAM-1 antibodies of the present invention exhibit substantially improved serum half-lives relative to native antibody. Thus, their administration to a recipient provides that recipient with an effective concentration of antibody over a longer time span than does the administration of non-poly (ethylene) glycol-modified anti-ICAM-1 antibody.

The antibodies of the present invention may be used in the same manner as LFA-1 or non-poly(ethylene) glycol-modified anti-ICAM-1 to treat inflammation caused or influenced by ICAM-1 mediated cellular adhesion. Such inflammation includes conditions that result from reactions of the specific or non-specific defense systems. A "specific defense system reaction" is a response of the immune system to the presence of specific antigens. A "non-specific defense system reaction" is a response mediated by leukocytes incapable of immunological memory. Such cells include granulocytes and macrophages Conditions that result from reactions of the specific defense system that may be treated with the antibodies of the present invention include inflammation resulting from autoimmune diseases, responses to antigens (such as rubella virus), delayed type hypersensitivity response mediated by T-cells (as seen, for example in individuals who test "positive" in the Mantaux test), etc. Conditions that result from reactions of the non-specific defense system that may be treated with the antibodies of the present invention include inflammation associated with conditions such as: asthma; adult respiratory distress syndrome (ARDS)or multiple organ injury syndromes secondary to septicemia or trauma; reperfusion injury of myocardial or other tissues; acute glomerulonephritis; reactive arthritis; dermatoses with acute inflammatory components; acute purulent meningitis or other central nervous system inflammatory disorders; thermal injury; hemodialysis; leukapheresis; ulcerative colitis; Crohn's disease; necrotizing enterocolitis; granulocyte transfusion associated syndromes; and cytokine-induced toxicity.

As indicated, the modified antibodies of the present invention may be used to block ICAM-1 molecules that are arrayed on the surfaces of endothelial and other cells. Since ICAM-1 is the cellular receptor to which the human rhinovirus binds in order to initiate rhinoviral infection (Greve, J. M. et al., Cell 56:839–847 (1989); Staunton, D. E. et al., Cell 56:849–853 (1989); Ohlin, A. et al., Antimicrob. Agents Chemother. 38:1413–1415 (1994); Cassanovas, J. M. et al., J. Virol. 68:5882–5889 (1994)), binding to endothelial cells of the nasal cavity, trachea and/or lungs inhibits rhinoviral infection. Thus the modified antibodies of the present invention provide a method of preventing new rhinoviral infection, as well as a method of treating existing infection (by permitting the infection of non-infected cells that are exposed to the virus shed from infected cells.

Having now generally described the invention, the same will be more readily understood through reference to the following examples which are provided by way of illustration, and are not intended to be limiting of the present invention, unless specified.

EXAMPLE 1

Poly(ethylene) Glycol-Modification of Anti-ICAM-1 Antibody

Clinical grade enlimomab was obtained from Dr. Karl Thomae, GmbH. Activated mPEGs were obtained from Shearwater Polymers, Inc. (Huntsville, Ala.). All mPEGs used in these experiments were an N-hydroxysuccinimidyl derivative of mPEG propionic acid (SPA-PEG) of molecular weight 5 kD (cat #M-SPA-5000). This activated mPEG is reactive toward amino groups on proteins. The chromatographic resin used to produce the sICAM-1 affinity column was the Emphaze Biosupport Medium AB1 from 3M. Buffer salts were "Ultra Pure" grade from 3M Sciences and water used in all experiments was produced by a Barnstead Nanopure water system having a resistance >17MΩ-cm.

Poly(ethylene) glycol-modified anti-ICAM-1 antibody enlimomab was prepared using either the solution or column poly(ethylene) glycol-modification method. For the solution poly(ethylene) glycol-modification method, conjugates of mPEG and enlimomab were produced in solution by mixing various ratios of activated mPEG and enlimomab in buffered aqueous solution. Reactions were quenched at various time points by adding diglycine to the reaction mixture to a 50 fold molar excess of over the available amino groups on enlimomab. Reaction contaminants (e.g., unreacted mPEG, diglycine, etc.) were removed from the reaction mixture by either diafiltration or dialysis, and buffer exchanged into 50 mM sodium phosphate, 100 mM sodium chloride, pH 6. Solutions were sterile filtered prior to storage at 4° C.

For the column poly(ethylene) glycol-modification method an sICAM-1 affinity column was prepared using Emphaze activated chromatography resin (azlactone chemistry). sICAM-1 was diafiltered into coupling buffer (860 mM Na$_3$Citrate, 100 mM NaHCO$_3$, pH 8.6) and the concentration adjusted to approximately 10 mg/ml. Emphaze Biosupport Medium was then added to the solution to give ~1 ml of swollen resin for each 20 mg of sICAM-1. The resin was mixed into the sICAM-1 solution with vortexing and the suspension was gently agitated for 1 hour at room temperature. Uncoupled sICAM-1 was removed by washing the resin ten times with one equal volume of PBS (50 mM sodium phosphate, 100 mM NaCl), pH 6, in a 125 mm sintered glass fritted tube. Unreacted azlactone groups were quenched by gently mixing the resin twice with 1 volume of 3M ethanolamine (pH 9), first for 30 minutes and then for 2 hours. The resin was then washed ten times with one volume of 1M NaCl followed by three times with one volume of PBS, pH 6. The resin was packed into a chromatographic column, washed with three column volumes of storage buffer (64 mM sodium phosphate, 86 mM NaCl, 2% (v/v) glycerol, 0.05% sodium azide, pH 6) and at stored at 4° C. To determine the coupling efficiency of the sICAM-1 to the Emphaze resin, the amount of unbound sICAM-1 from the coupling reaction was quantitated using the BCA method. The capacity of the sICAM-1 affinity column was determined by sequentially loading the column until breakthrough of enlimomab was observed.

The sICAM-1 affinity column was equilibrated with 5 column volumes of PBS, pH 7.5, and the column was loaded to capacity with enlimomab (2–5 mg/ml in PBS, pH 7.5). A solution of activated SPA-PEG (5 kD) was prepared in one column volume of PBS, pH 7.5. The mPEG solution contained one milligram of mPEG for every milligram of enlimomab loaded onto the sICAM-1 column. The mPEG solution was recycled over the sICAM-1 column for one hour at room temperature and removed by washing the column with five volumes of equilibration buffer. The mPEG-enlimomab was then eluted with two column volumes of either: 100 mM glycine, pH 2.7, and then neutralized with 1M Tris-base, pH 9, or 100 mM sodium carbonate (pH 11), and then neutralized with 1M sodium phosphate (pH 4.5).

Experiments to modify enlimomab with PEG have been performed using the succinimidyl ester of carboxymethylated PEG 5000 MW (SCM-PEG) or succinimidyl propionate (SPA-PEG). Enlimomab has also been derivatized using the 20,000 MW analogs of these 2 derivatives. These and other coupling chemistries have also been tried at 5000 MW, 20,000 MW and 40,000 MW.

In sum, the enlimomab monoclonal antibody was modified with the SPA and SCM derivatives by reacting dry weighted mPEG derivative with a solution of the antibody for a short defined period of time at 4° C. The pH of reaction solutions was maintained with low ionic strength phosphate buffer over the pH range of 6.0–8.0. Reactions at higher pH were performed in a 50 mM borate buffer. Ratios of protein to mPEG derivative ranged from 10:1 to 1:10. Thus, in some instances there was an excess of lysines, making the m-PEG the limiting reagent (and causing a low degree of modification). At the other extreme where there was an excess of m-PEG, the lysines were limiting (and a high degree of modification occurred). Concentrations of enlimomab protein solutions ranged from 1 mg/ml to 10 mg/ml. Reactions involving the SPA derivative were quenched with an excess of concentrated diglycine, while it was not necessary to quench the SCM reactions due to the short half-life. Excess and unreacted PEG was diafiltered at least 3× using Amicon 30 kD or 100 kD centriprep devices.

EXAMPLE 2

Analytical Methods for the Purification of Poly (ethylene) Glycol-Modified Anti-ICAM-1 Antibody Analytical methods for purifying poly(ethylene) glycol-modified anti-ICAM-1 antibody were developed. The objectives of this effort were two-fold: (1) to develop a hydrophobic interaction chromatography method which would allow for the rapid characterization of poly(ethylene) glycol-modified preparations of the monoclonal antibody Enlimomab; and (2) to provide a general approach to purify PEG-modified proteins. Chromatographic testing was performed using several commercially available HIC columns: Synchropak (purchased from Synchrom Inc., Lafayette, Ind.), Hydropore HIC columns (from Rainin Instrument Co. (Emeryville, Calif.), or Bio-Gel TSK phenyl-5-PW (purchased from Bio-Rad, Hercules, Calif.).

A series of enlimomab poly(ethylene) glycol-modified derivatives was used in assessing each HIC column. These conjugates varied in degree of poly(ethylene) glycol-modification, chemistry of coupling and molecular weight of PEG derivative used in the coupling procedures. The derivatives ranged from mixtures which still had as much as 35% remaining native antibody as determined by other techniques to mixtures devoid of native and having poly (ethylene) glycol-modified species with as many as 30 PEG-5000 units per antibody molecule. This wide range in sample compositions enabled a thorough assessment of the separation capability of each column.

Analytical HIC was performed on the Hewlett-Packard 1050 system, consisting of multi-wavelength detector 1050, quaternary pump with high tech piston wash system, auto injector, 100 µl injection loop (also 2.0 ml prep loop). Protein concentration was monitored by following UV adsorbance at 280 nm. Data storage was handled with the HP Chemstation software run on a Vectra 486/33M personal computer Chromatograms were printed on an HP Deskjet Plus printer and stored on the hard drive for archiving. The nature of the poly(ethylene) glycol-modified products were determined by electrophoresis. Electrophoresis was performed using both the Novex system and the Pharmacia Phastsystem. Non-reduced SDS-PAGE gels were of the following type and composition. Phastgels, 4–15% gradients, were run on the Pharmacia Phastsystem, with 1 microliter sample application. Protein concentration varied from 1–10 mg/ml.

Preliminary experiments were performed using a low salt concentration isocratic HIC HPLC system. These experiments served as an initial screen for relative hydrophobicity of the native Mab as well as poly(ethylene) glycol-modified enlimomab preparations. While multiple peak separations were seen with some sample/column combinations, no trend emerged favoring one column chemistry over another. Therefore a gradient HPLC method was developed.

The initial survey of hydrophobic interaction columns was performed using a very simple reverse salt gradient 2M $(NH_4)_2SO_4$ in 100 mM phosphate pH 7.0 to 0M ammonium sulfate in 100 mM phosphate pH 7.0. The gradient was run over 10 column volumes; all columns were 4.6×100 mm (1.66 ml) with the exception of the Phenyl-5-PW column which is only available in a 7.5×75 mm (3.3 ml) or larger format; flow rate was 1.0 ml/min.

The Synchropak Hydroxy-propyl HIC resin was evaluated first. Chromatograms of enlimomab and poly(ethylene) glycol-modified enlimomab were obtained under simple gradient conditions (15 minutes from 0–100% B). These samples were classified based on chromatographic behavior on SEC, SDS-PAGE and TNBS assay (to determine number of free amine) as ranging from mild to moderately poly (ethylene) glycol-modified. Native content ranges from <5% to 35% as estimated from a combination of HPLC SEC and non-reduced SDS-PAGE. None of these samples exhibited any degree of separation of native from poly(ethylene) glycol-modified species. However, there was a marked difference in peak shape for the various samples.

Several much more highly poly(ethylene) glycol-modified samples were chromatographed using the same simple gradient on the Synchropak hydroxy propyl column. The sample of SPA-20 KD reaction mixture was resolved into two peaks, native enlimomab and a second peak at a longer retention time, thus a more hydrophobic species is separated. However, upon examination of HPLC-SEC chromatograms of this sample, this much more hydrophobic species represented only a small subspecies of very highly poly(ethylene)glycol-modified enlimomab. The majority of 20 KD poly(ethylene) glycol-modified enlomomab was not resolved from native unmodified antibody on the hydroxypropyl column. Two other samples which were very highly poly(ethylene) glycol modified (1:5 and 1:10 ratios of enlimomab:mPEG respectively) showed a shift to much longer retention times of a single species with increasing ratios of PEG. However, there was still no separation of residual native enlimomab in these highly poly(ethylene) glycol-modified preparations.

The results obtained in the chromatography of the mild to moderately poly(ethylene) glycol-modified enlimomab preparations provided evidence that separation could be achieved between native and poly(ethylene) glycol-modified enlimomab species.

A slightly more hydrophobic ligand was tested in an attempt to facilitate the separation of native enlimomab from poly(ethylene) glycol-modified adducts. Some of the previous chromatographic experiments were repeated using the Synchropak Methyl HIC column. This time only a moderately poly(ethylene) glycol-modified enlimomab derivative (a 5:1 wt./wt ratio) was chromatographed. This column ligand was unable to resolve the native antibody from its poly(ethylene) glycol-modified derivative even when the gradient was extended to 30 minutes (equivalent to approximately 20 column volumes). With a 20 column volume gradient, the best that could be achieved was the beginnings of a shoulder in the chromatogram for the poly(ethylene) glycol-modified enlimomab sample. The incremental increase in ligand hydrophobicity from hydroxy propyl to methyl failed to improve the separation between native and poly(ethylene) glycol-modified enlimomab species. Similar results were obtained when the next ligand in the Synchrom series, propyl, again slightly more hydrophobic than the previous ligand was tested with the same sample set as before.

The last alkyl chain ligand in the Synchrom series, pentyl was also tested in a similar manner as that used with the other columns but proved to be too hydrophobic to allow release of enlimomab even at the end of the gradient. In this chromatographic run the native enlimomab antibody was not eluted even at 100% B buffer (100 mM phosphate buffer, pH 4.5). In fact it was necessary to use water with no added salt in order to elute enlimomab from the pentyl column.

Since increasingly more hydrophobic ligands in the alkyl chain series had no positive effect on resolution, a different type of chemistry, phenyl, was investigated. The phenyl group is approximately as hydrophobic as a propyl group based on size, but has the added component of pi-pi interactions through its phenyl ring. Gradient HIC-HPLC method development utilizing the BioRad Phenyl 5-PW column (7.5×75 mm, 3.3 ml column volume) was conducted. Chromatographic gradient runs were performed on the phenyl column using both the standard 15 minute linear reverse salt gradient (5 column volumes) and a 30 minute linear gradient (10 column volumes). While a 5 column volume gradient was not sufficient to provide adequate separation of native enlimomab from poly(ethylene) glycol-modified species, the heterogeneity of the various samples was demonstrated using the phenyl column. With the employment of a 10 column volume gradient, there was marked improvement in chromatographic resolution as evidenced by the separation of both native enlimomab and the poly(ethylene) glycol-modified species and from the resolution of multiple PEG-enlimomab adducts. HIC employing the phenyl ligand was capable of revealing some heterogeneity in poly(ethylene) glycol-modified samples of enlimomab. This column showed great potential in its ability to separate native enlimomab from poly(ethylene) glycol-modified forms of enlimomab. The change from the alkyl ligand series to phenyl provided enough selectivity to reveal the heterogeneity of the poly(ethylene) glycol-modified enlimomab preparations.

Better selectivity and resolution were obtained when a more unique hydrophobic resin HIC method was conducted. This method employed Rainin's Hydropore column, which is only mildly hydrophobic. The Hydropore column fortuitously has PEG as its hydrophobic ligand. It was hoped that the mechanism of interaction seen in 2-phase systems which incorporate PEG would hold true in the chromatographic separation, and that the use of this ligand would permit the separation of native protein from PEG modified protein. The initial chromatographic runs were performed under identical conditions to those used on the other HIC columns utilizing the same samples.

Chromatograms from some of the mild to moderately poly(ethylene) glycol-modified samples displayed a shift in retention time (to greater hydrophobicity) for most of the samples; the least modified sample pool shows significant resolution between the native species and what are apparently 2 different PEG modified species. When this sample was tested on other HIC columns no separation at all was detected, nor was any significant change in retention time relative to the native antibody identified. Thus some degree of separation of native enlimomab from PEG-modified adducts has been effected on this column.

For samples which are moderately poly(ethylene) glycol-modified, no native enlimomab was detected by this chromatographic technique on the Hydropore HIC column. However, the retention times of eluting species was greater than native enlimomab by two (2) minutes.

When much more highly poly(ethylene) glycol-modified samples were tested using the Hydropore HIC column system, there was a dramatic change in the retention behavior of the PEG derivatives relative to the native enlimomab. With more highly poly(ethylene) glycol-modified species of enlimomab, such as the SCM-5 KD 1:10 poly(ethylene) glycol-modified species, the retention time increased by 3 minutes or 2 column volumes and the chromatographic peaks were quite sharp relative to less modified samples. On a 15 minute, 10 column volume gradient, this amounted to a difference in eluting salt of 400 mM, and represented a tremendous change in hydrophobicity between the poly (ethylene) glycol-modified enlimomab and the native antibody.

The SPA-20 KD reaction mixture illustrates the difference in hydrophobicity when a single PEG strand of 20 KD is attached to enlimomab versus multiple strands of 5 KD. With baseline resolution between the native and 20 KD poly(ethylene) glycol-modified species, quantitation of residual unmodified enlimomab was straightforward. The SDS-PAGE gel and SEC chromatogram of the 20 KD sample corroborated these results. Separation seen previously on the hydroxypropyl column indicated that native enlimomab and 1-20 KD PEG-enlimomab were equivalent in hydrophobicity (as they co-eluted) and that the second peak at a retention time of 10.29 minutes was the 2-PEG derivative.

Having demonstrated the utility of the Hydropore HIC column in separating native enlimomab from poly(ethylene) glycol-modified adducts for a variety of preparations, a more thorough study was conducted to determine the limits of the methods. A series of SCM-5000 enlimomab derivatives ranging from lightly to very heavily modified with ratios varying from 10:1 at the low end up to 1:1 at the very high end were prepared.

Results of Hydropore HIC in quantitating residual native enlimomab in these samples are presented in Table 1. It is possible to detect native enlimomab at a less than 1% level and at levels above 40% based on this preliminary ranging study.

TABLE 1

| Ratio of Enlimomab to SCM Activated PEG (mg/mg) | % Native |
| --- | --- |
| 10:1 | 41.2 |
| 5:1 | 18.3 |
| 4:1 | 9.9 |
| 3:1 | 5.4 |
| 2:1 | 0.6 |
| 1:1 | none detected |

The above-described HIC analysis using the Hydropore column permitted the determination of the percentage of native enlimomab remaining in the reaction as a function of ratio of PEG/enlimomab in the reaction mixture. Selected chromatograms from the SCM-5000 series were obtained. These chromatograms illustrate the changes in chromatography seen as a function of increasing degrees of poly (ethylene) glycol-modification of native enlimomab. In the least poly(ethylene) glycol-modified sample, SCM-5000 10:1 there remains 41.2% native enlimomab and the poly (ethylene) glycol-modified species are seen mainly as a single major peak of increased hydrophobicity with the hint of a shoulder for a second poly(ethylene) glycol-modified species. Corroborating evidence for this identification of peaks was obtained from non-reduced SDS-PAGE. The SCM-5000 10:1 sample separated in such SDS-PAGE into the native enlimomab, a major 1-PEG species and a minor 2-PEG species. Several other samples from the SCM-5000 series were also electrophoresed in the same manner with a corresponding correlation between non-reduced SDS-PAGE gel electrophoresis and Hydropore HIC chromatography. These results demonstrate that the above-described chromatographic technique is useful in determining native enlimomab in poly(ethylene) glycol-modified preparations.

The Hydropore HIC columns are presently available in either a 12 μm particle size or a 5 μm particle size. Generally one can expect an increase in back pressure as a function of the decrease in particle size. This holds true for a reverse phase HPLC system using small molecules as models. However, the increase in resolution with respect to the separation of proteins as a function of particle size is much more modest. Thus one would not expect a tremendous improvement in HIC separation in going from a 12 μm particle to a 5 μm particle and that was the case with the Hydropore HIC packing material. There was modest improvement seen in the resolution between native enlimomab and the 1-PEG species as well as improvement in separation between the individual 1-PEG, 2-PEG, 3-PEG etc. species. The general trend was an overall increase in peak sharpness in going from the 12 to the 5 μm particle due to the increase in theoretical plate counts for the smaller particle size column.

While the initial experiments used in developing this method were performed on the 12 μm particles, the SCM-5000 poly(ethylene) glycol-modified series was repeated with the 5 μm particle column. For routine analytical samples, the 5 μm particle column was adopted due to the improved separation of native enlimomab from the poly (ethylene) glycol-modified species. This technique was also useful for profiling the poly(ethylene) glycol-modification reactions for reproducibility of heterogeneity and as a stability indicating method. These same results were achievable in many cases with the 12 μm particle material depending on the the poly(ethylene) glycol-modification chemistry, molecular weight of the PEG derivative and the hydrophobicity of the native protein relative to its poly(ethylene) glycol-modified derivatives. Even though the 5 μm particle Hydropore columns achieved greater resolution than the 12 μm particles adequate separations could be attained with the larger particles at significantly reduced back pressures, an important factor in scaleup.

As another example of the utility of this technique in separating native protein from poly(ethylene) glycol-modified species, the time course of a poly(ethylene) glycol-modification reaction was monitored using the Ald-5000 PEG derivative coupling to a Fab of another antibody. This reaction was followed over a 24 hour period. The Fab was less hydrophobic than enlimomab, eluting at 7.14 minutes versus 9.54 minutes (15 min. linear gradient) and that the poly(ethylene) glycol-modified Fab, with a single 5000 MW PEG attached was significantly more hydrophobic than the native molecule eluting at 9.70 minutes. In this case 1-PEG-Fab species could be readily separated from the native Fab and the quantiation of residual native protein was straightforward as baseline resolution was achieved. But since baseline resolution is not achieved between native enlimomab and the poly(ethylene) glycol-modified species, improvements were made to the original gradient in an attempt to remedy this situation before proceeding to scaling the method for use in purification.

Starting with the 15 minute linear gradient on the 12 μm particle size Hydropore 4.6×100 mm column which was approximately 10 column volumes, the gradient was extended to 30 minutes or about 20 column volumes and then to 60 minutes or 40 column volumes with the SCM-5000 5:1 preparation as a test mixture. While it might not be practical to have an analytical method with a 60 minute gradient for multiple samples per day, such gradients did demonstrate a simple means to improve the resolution between native enlimomab and the poly(ethylene) glycol-modified species. As a compromise between improved resolution and method efficiency a 30 minute gradient was run starting the gradient at 50% B and linearly changing to 100% B. While the separation of native enlimomab from the poly(ethylene) glycol-modified species was almost as good as seen in the 60 minute gradient, 30 minutes in run time was saved. With this improved higher resolution method enlimomab-PEG reaction mixtures were then fractionated into individual 1-PEG, 2-PEG, 3-PEG, etc. species. These now homogeneous poly(ethylene) glycol-modified adducts were thoroughly analyzed for binding activity using a competitive specific ELISA (relative to native enlimomab), by SEC, nonreduced and reduced-SDS PAGE and rechromatographed on Hydropore HIC to determine purity.

In sum, native (i.e., non-poly(ethylene) glycol-modified) material present in the crude mPEG-enlimomab mixture of Example 1 was removed from mPEG-enlimomab preparations by a hydrophobic interaction technique which would allow the rapid characterization of poly(ethylene) glycol-modified preparations of the monoclonal antibody enlimomab and provide a general approach to analyzing such modified proteins.

The very unique properties of the Hydropore ligand permitted not only the separation of native enlimomab from poly(ethylene) glycol-modified enlimomab but also the fractionation of individual poly(ethylene) glycol-modified species which varied in the number of poly(ethylene) glycol units attached. This high resolution technique was used to separate native enlimomab from poly(ethylene) glycol-modified enlimomab as well as for fractionating the individual species for further characterization. Hydropore was used analytically for characterizing the poly(ethylene) glycol-modification process, for quantitation of native, 1-PEG, 2-PEG, 3-PEG etc. species and also for the purification of poly(ethylene) glycol-modified-enlimomab on a larger scale (up to 500 mg).

Samples which are highly poly(ethylene) glycol-modified were found to be free from residual native PEG as determined by chromatograms and electropherograms. In addition to being able to quantitate native antibody in poly (ethylene) glycol-modified samples this method also provides a fingerprint of the poly(ethylene) glycol-modification reaction and can be used in quality control for batch-to-batch variability testing. Since it is possible to determine the area of individual peaks by this method using the HP chemstation software one can also use this technique to monitor stability of poly(ethylene) glycol-modified proteins, monitor the progress of poly(ethylene) glycol-modification reactions over a time course, etc. An important use of this method is its utilization to determine the percent of residual non-poly(ethylene) glycol-modified protein in a preparation which would eventually be used in either immunogenicity trials or pharmacokinetic studies where the objective of poly(ethylene) glycol-modification is to increase the half-life of small proteins or reduce immunogenicity of native protein. Once it has been determined that there is residual native protein in a poly(ethylene) glycol-modification preparation it is then possible to remove the native protein from the poly(ethylene) glycol-modification preparation. This task may also be accomplished using the same Hydropore HIC column material.

EXAMPLE 3

Preparative Methods for the Purification of Poly (ethylene) Glycol-Modified Anti-ICAM-1 Antibody Due to the column modules' design it was very easy to scale the HIC method from an analytical level to a preparative scale level. Thus, for example, an analytical method developed on a 4.6×100 mm column could be readily transferred to a 21.4×100 mm column where purification of hundreds of mg can be achieved in a single chromatographic run. Initial purifications runs were conducted using a Hydropore 10.0×100 mm column.

Large scale purifications were performed on a chromatographic system of the following composition: 2 Waters 590 pumps, a Waters 680 gradient controller, and a Kratos 773 multi-wavelength detector. Samples were injected using a Rheodyne 9125 six-port injection valve using either a 5.0 or 20 ml PEEK loop. Chromatographic data was collected through an A-D link to our in-house LAS, laboratory automation system. Table 2 shows the scale up parameters.

TABLE 2

| Size (mm) | Volume (ml) | Max ml/min. | Scale | Capacity (mg) |
|---|---|---|---|---|
| 4.6 × 100 | 1.66 | 4.0 | 1.0 | 20 |
| 10.0 × 100 | 7.85 | 15.0 | 4.7 | 100 |
| 21.4 × 100 | 36.0 | 65.0 | 21.6 | 450 |
| 41.4 × 100 | 135 | 300.0 | 81 | 1600 |

It has been possible to effect an even greater degree of separation between the native antibody and PEG-derivatized species via the incorporation of a isocratic salt hold step at an appropriate point in the gradient. Just at the point in the gradient (50% Buffer B) when the native enlimomab starts to elute, these conditions are held for an additional 2 column volumes, after which the gradient is continued out to 100% Buffer B. This separation is shown by non-reducing SDS-PAGE in which the band corresponding to native antibody is virtually absent.

To purify the poly(ethylene) glycol-modified enlomomab, the crude mPEG-enlimomab reaction mixture produced by the column process was applied to the HIC column in 2M ammonium sulfate, 100 mM phosphate, pH 6, and a step gradient was run from 2M to 0.5M ammonium sulfate. The native enlimomab eluted first as the ammonium sulfate concentration approaches 0.9M, and the poly(ethylene) glycol-modified antibody derivative eluted in later fractions.

EXAMPLE 4

Purification of Poly(ethylene) Glycol-Modified Enlimomab

The eluates of several runs were pooled and concentrated to 15 mg/ml. This crude pool was then applied to a preparative Superdex 200 size exclusion chromatography column. The single broad peak that emerged was fractionated to remove both ends, the front end containing heavily poly (ethylene) glycol-modified enlimomab and the late tail end containing lightly poly(ethylene) glycol-modified and native enlimomab.

In evaluating HIC resins for the purification of poly (ethylene) glycol-modified enlomomab, the anticipated final scale should be considered. The ideal resin will exhibit strong mechanical integrity and chemical resistance, have good protein capacity and be commercially available in a format applicable to medium-low pressure purification techniques and equipment in addition to providing comparable selectivity to the silica based material used in laboratory scale purifications.

Poros HP, PH, PE, BU and ET are polymeric packings designed for hydrophobic interaction chromatography (HIC) of peptides, proteins and other biomolecules in the Perfusion Chromatography mode. The packings consist of crosslinked polystyrene/divinyl benzene flow-through particles with a patented bimodal pore size distribution for very rapid mass transport. The particles are surface coated with a crosslinking polyhydroxylated polymer. This coating is further functionalized with phenyl groups (POROS HP and PH), phenyl ether groups (POROS PE), butyl groups (POROS BU) or ether groups (POROS ET).

While all of the Poros HIC resins meet the desired profile, the Poros 50 µ particle, because it is commercially available, is preferred. This resin was tested, using a preparation of poly(ethylene) glycol-modified enlimomab, for its ability to separate native enlimomab from poly(ethylene) glycol-modified enlimomab.

The initial experiment involved the injection of 100 µl samples of a poly(ethylene) glycol-modified enlimomab preparation directly onto a 4.6×100 mm analytical Poros PE HIC using a BioCad 60 Workstation. A simple 10 column volume linear reverse salt gradient from 2M-5M ammonium sulfate (100 mM phosphate, pH 6.0 background) was used to test the selectivity of the Poros PE resin. Under these chromatographic conditions if multiple peaks are observed optimization of the method can be achieved utilizing the extensive capabilities of the BioCad workstation. The general BioCad parameters are outlined in Table 3 below:

TABLE 3

| Flow Rate (ml/min) | Velocity | Line A | Line B | Line C | Line D |
|---|---|---|---|---|---|
| 10.0 | 3600 | 1.0M pH 6.0 | 1.0M pH 8.0 | Water | 3M $(NH_4)_2SO_4$ |

The BioCad buffers are configured in the pH mode with starting conditions of 100 mM sodium phosphate pH 6.0, 2M ammonium sulfate. The gradient was programmed to change from 2M ammonium sulfate to 0.5M in a linear fashion over 10 column volumes, the 100 mM phosphate pH 6.0 is a constant throughout the course of the chromatographic run. The chromatogram showed two peaks as the result of the simple 10 column volumes gradient. This demonstrates the selectivity of the resin Poros PE in its ability to separate native enlimomab from poly(ethylene) glycol-modified enlimomab. Multiple chromatographic runs were performed using this simple gradient with fractions of peak 1 and peak 2 being collected and analyzed. The analysis proved that peak 1 was comprised of native enlimomab while peak 2 was the composite of poly(ethylene) glycol-modified enlimomab species. Further method development led to a procedure which improves baseline resolution of native enlimomab from the composite of $PEG_n$-enlimomab adducts.

The optimized HIC method involves 2 distinct gradients with an isocratic hold step positioned at a salt concentration which allows maximum separation of native unpoly (ethylene) glycol-modified enlimomab from $PEG_n$-enlimomab adducts. The method comprises the following steps:

1. column equilibration
2. loading of sample preparation
3. wash of column with equilibration buffer 4. gradient I 2M–0.9M $(NH_4)_2SO_4$ in 5 column volumes
5. 0.9M hold for 10 column volumes
6. gradient II 0.9M–0.5M $(NH_4)_2SO_4$ in 2 column volumes
7. 0.5M hold for 5 column volumes
8. gradient change to equilibration buffer 100 microliters of a enlimomab poly(ethylene) glycol-modified preparation was injected onto the Poros PE column. enlimomab elutes during the 0.9M hold step and is clearly separated from PEG-enlimomab which is eluted during the second gradient between 0.9M and 0.5M ammonium sulfate. This optimized method developed on an analytical Poros PE 4.6×100 mm column was then scaled up for purification using a larger format Poros 20 PE column.

A larger column was prepared for scaleup purification of poly(ethylene) glycol-modified enlimomab utilizing Waters' AP glass column system designed for medium to high pressure systems. Poros PE 20 micron media is intended for use with BioCad or HPLC systems as the backpressure generated with small particles (20 um) exceeds low pressure system limits. A 2.0 cm×19.8 cm bed Poros 20 PE column of 62 ml volume was packed using the BioCad system. Packing buffer was deionized water at a flow rate of 50 ml/min. Back pressure did not exceed 500 psi during the packing process. The essential elements of the method remained unchanged at this scale with the exception of preparation of poly(ethylene) glycol-modified enlimomab solution for column loading. Since it was desired to capture as much protein as possible during the column loading step it, 3M ammonium sulfate was added to the poly(ethylene) glycol modification reaction solution prior to loading. By careful addition of the concentrated salt of the poly(ethylene) glycol modification reaction mixture it was possible to reach conditions which facilitated the capture of 100% of the protein mixture. From this point on the method was identical to the small scale chromatography procedure described above. A chromatogram from a BioCad run on the 62 ml Poros 20 PE column revealed that enlimomab eluted during the initial isocratic hold step and PEG-modified enlimomab adducts eluted as a single peak during the second gradient portion of the method.

A coomassie-stained non-reduced SDS-PAGE gel of the eluted materials indicated that a small amount of mono-PEG-enlimomab eluted during the isocratic hold step (in which the native enlimomab elutes). It was possible to obtain fractions that consisted of PEG-modified enlimomab adducts with no residual non-poly(ethylene) glycol-modified native enlimomab. Thus the scaleup to a larger column format with Poros 20 PE resin was successful. This scale allows for relatively large amounts of poly(ethylene) glycol-modified enlimomab to be prepared using the BioCad or HPLC systems. In order to meet the additional requirements of a large scale purification while relying on low pressure chromatographic equipment, scaleup with Poros PE media using 50 micron particles was undertaken.

Poro PE hydrophobic interaction chromatography media has been supplied in a 50 µm format which allows its usage in low pressure systems. An Upchurch Scientific's Omega series 10.0×100 mm peek column was packed with 7.85 ml of this new media. Testing of the HIC method developed for the Poros PE 20 micron material with the 50 um particle Poros PE lead to some modifications due to a difference in hydrophobic ligand coverage between the 2 resins. The larger particles appeared to be less hydrophobic since native enlimomab eluted at a higher ammonium sulfate concentration on the Poros 50 PE than the Poros 20 PE resin.

The method developed for Poros 50 PE differed from the Poros 20 PE method only in the concentration of ammonium sulfate which was required to elute native enlimomab. This change prompted corresponding changes in the gradients and first hold step which reflect the concentration of ammonium sulfate required to elute enlimomab. The result of these changes did not however affect the chromatographic separation of native enlimomab from poly(ethylene) glycol-modified enlimomab as compared to Poros 20 PE chromatography. Table 4 provides a summary of HIC results on the Poros PE column. The column was run near maximum column pressure.

TABLE 4

| Dimensions (mm) | 4.6 × 100 | 20 × 198 | 16 × 52 |
|---|---|---|---|
| Volume (ml) | 1.66 | 62 | 10 |
| Flow (ml/min) | 10 | 50 | 20 |
| linear (cm/hr) | 3600 | 950 | 600 |
| pressure (psi) | 1500 | 900 | 70 |
| particle (µm) | 20 | 20 | 50 |
| Hold step cond (mS) | 89 + 2 | 91 + 2 | 103 |

In accordance with this method mPEG-enlimomab produced in solution was purified using a commercially available hydrophobic interaction chromatography (HIC) resin. The crude mPEG-enlimomab reaction mixture was applied to the HIC column equilibrate with 2M ammonium sulfate 100 mM phosphate, pH 6 buffer. Ammonium sulfate concentration was adjusted in the poly(ethylene) glycol-modification reaction mixture prior to column loading to ensure complete retention to the Poros PE hydrophobic interaction matrix. A reverse salt step gradient was run with the native enlimomab eluting first as the ammonium sulfate concentration is reduced to 0.9M and held at this level for an additional 10 column volumes. During the second gradient step, the salt concentration is dropped further to 0.5M and the mPEG-enlimomab is eluted from the column as a single peak.

The purity and identity of poly(ethylene) glycol-modified enlimomab may be measured using a combination of analytical methods including, analytical HIC, reducing and non-reducing sodium dodecyl sulfate polyacrylamide gel electrophoresis (SDS-PAGE) and size exclusion chromatography. Densitometric scanning of non-reduced Coomassie-stained SDS-PAGE gels allow estimation of the relative band areas of each poly(ethylene) glycol-modified species of BIRR10. Reduced SDS-PAGE gels provide information on location and distribution of PEG strands on the heavy and light chains of enlimomab.

If the mixture of poly(ethylene) glycol-modified and non-poly(ethylene) glycol-modified material is processed accordingly and analytical hydrophobic interaction chromatography is performed, no native non-poly(ethylene) glycol-modified material can be detected.

EXAMPLE 5

Competitive ELISAs for Anti-ICAM-1 Antibody

Two competitive ELISAs were used to characterize the poly(ethylene) glycol-modified antibody, and to assess its in vitro potency. The first competitive ELISA based upon the sICAM-1 antigen (sICAM-1) recognized by enlimomab was used to compare the binding constants of various mPEG-enlimomab derivatives to that of native ("unpoly(ethylene) glycol-modified") enlimomab. Microtiter plates (96 wells) were coated with a solution of 10 µg/ml sICAM-1 in PBS, pH 7.1 (100 µl/well). Open sites on the plates were then blocked with 250 µl/well of 1% BSA solution in PBS, pH 7.1. To minimize the effect of plate-to-plate variability, a competition was run between biotinylated-enlimomab and enlimomab and biotinylated-enlimomab and mPEG-enlimomab on each microtiter plate. The concentration of biotinylated-enlimomab was held constant at 2.5 µg/ml. enlimomab and mPEG-enlimomab were diluted 1:3 across the plate beginning with column 2 at 80,000 ng/ml and ending at 1.4 ng/ml in column 12. After overnight incubation, the plates were washed and each well was incubated for 90 minutes with 100 µl of a 1:5,000 dilution of streptavidin-horseradish peroxidase. Plates were washed and color was developed by adding 100 µl of an O-phenylenediamine solution to each well. The color development was stopped by adding 100 µl/well of 2N $H_2SO_4$ and the absorbance of each well was read at 490 nm. Data were analyzed using a non-linear SAS routine. A binding activity for each mPEG-enlimomab derivative relative to enlimomab was determined by comparing the binding constant of the mPEG-enlimomab derivative with that of enlimomab on each plate. A minimum of 3 plates were run to determine the relative binding activity of each mPEG-enlimomab derivative.

In addition to the sICAM-1 based ELISA, a competitive ELISA based on whole human JY cells was utilized. In this assay, human JY cells which express ICAM-1 on their surface were coated on each microtiter plate rather than coating the plates with sICAM-1. The competition reactions, color development and data analysis were essentially the same as the sICAM-1 ELISA described above.

The sICAM-1 ELISA estimated a binding avidity constant for BIRR10 at 25% that of enlimomab while the JY cell avidity ELISA, representing a more appropriate measure, was 70% that of enlimomab.

EXAMPLE 6

Characterization of the Poly(ethylene) Glycol-Modification Reaction

The poly(ethylene) glycol-modification reactions of Example 1 were characterized in order to determine optimal reaction conditions.

To investigate the pH dependence of the mPEG/enlimomab reaction of Example 1, reactions were run at pH values of 7.0, 7.5 and 8.0. For all reactions the final concentration of enlimomab was 1 mg/ml, the mPEG:enlimomab ratio was at 1:1 on a weight-to-weight basis, and all reactions were run at 4° C. Aliquots were removed from each reaction and quenched at 1, 2, 3, 4, 5, 6, and 24 hours. To determine the degree of poly(ethylene) glycol-modification of enlimomab as a function of pH and time, Coomassie stained non-reducing SDS-PAGE gels were run of all aliquots. From this analysis, the mPEG/enlimomab reaction was found to be strongly pH dependent in the range investigated. At pH 8.0 no unpoly(ethylene) glycol-modified material was visible after only 2 hours, while at pH 7.0 native material remained in the reaction mixture even after 24 hours. Reaction mixtures containing little or no native material were selected for further analysis. Residual binding activity was determined for these samples using the sICAM-1 based competitive ELISA. These results are shown in Table 5.

TABLE 5

| Reaction pH | Reaction Time (Hours) | % Binding Relative to enlimomab |
|---|---|---|
| 7 | 24 | 20% |
| 7.5 | 4 | 11% |
| 7.5 | 5 | 9% |
| 7.5 | 6 | 7% |
| 7.5 | 24 | 2% |
| 8.0 | 1 | 12% |
| 8.0 | 2 | 3% |
| 8.0 | 3 | 0% |

To investigate the effect of the weight-to-weight ratio of mPEG to enlimomab on the conjugation reaction, six different reactions were run with ratios of mPEG:enlimomab ranging from 2:1 to 1:5. The final concentration of enlimomab in each reaction was 1 mg/ml. All reactions were run at pH 7.0, 4° C., for 24 hours. Each reaction was analyzed by non-reducing SDS-PAGE. Samples containing little or no native material were selected for further analysis. Residual binding activity was determined for these samples using the sICAM-1 based competitive ELISA. These results are shown in Table 6.

TABLE 6

| mPEG:enlimomab | Reaction Time (Hours) | % Binding Relative to enlimomab |
|---|---|---|
| 1:1 | 24 | 14% |
| 2:1 | 24 | 1% |

From results of the above studies, the following reaction conditions were chosen to produce poly(ethylene) glycol-modified enlimomab using the solution-based modification procedure: pH 7.0, 4° C., mPEG:enlimomab of 1:1, and a reaction time of 24 hours. Using these reaction conditions the process was scaled up to produce larger quantities of material. The enlimomab modified in this manner contained an average of from 2–10 poly(ethylene) glycol adducts.

With reference to the column-based method for introducing poly(ethylene) glycol modifications, the sICAM-1 was coupled to the Emphaze resin with an efficiency of approximately 90 to 98%, as determined by quantitating the unbound sICAM-1 in the resin wash solution using the BCA method. This corresponds to approximately 19 mg of covalently bound sICAM-1 for each milliliter of swollen resin. The binding capacity of the sICAM-1 affinity resin for enlimomab was determined as a function of pH. Results are shown in Table 7. These data show that in the pH range examined, each milliliter of sICAM-1-Emphaze resin has a binding capacity of approximately 8 mg of enlimomab.

TABLE 7

| Equilibrium pH | Total mg of enlimomab Bound | mg enlimomab/ml gel |
|---|---|---|
| 6.0 | 43 | 8.6 |
| 7.0 | 44 | 8.8 |
| 8.0 | 41 | 8.2 |

Eight poly(ethylene) glycol-modification runs were performed on a single sICAM-1 affinity column in order to assess the reproducibility of the method. The SDS-PAGE banding patterns obtained from each run were fairly reproducible and each reaction produced an mPEG-enlimomab conjugate with a similar degree of poly(ethylene) glycol-modification (i.e., average of 5 PEG 5 kD adducts). For each poly(ethylene) glycol-modification run, the enlimomab breakthrough during the load phase and the material eluted from the column after the poly(ethylene) glycol-modification reaction were collected. These materials were quantitated and an analytical SEC retention time was determined for each sample. It can be seen in Table 8 that the run to run retention time by analytical size exclusion chromatography (SEC) was very reproducible (<1% RSD), indicating that the column poly(ethylene) glycol-modification process is reproducible. In Table 8, "B" denotes breakthrough; "E" denotes elution; "ND" denotes not done.

TABLE 8

| Parameter | Run Number | | | | | | | |
|---|---|---|---|---|---|---|---|---|
| | 1 | 2 | 3 | 4 | 5 | 6 | 7 | 8 |
| SEC Retention Time (min.) | | | | | | | | |
| B | ND | ND | ND | 11.83 | 11.82 | 11.82 | 11.82 | 11.83 |
| E | 9.84 | 9.86 | 9.74 | 9.72 | 9.72 | 9.74 | 9.94 | 9.66 |
| mg Recovery | | | | | | | | |
| B | <0.2 | 1.5 | 2.4 | 2.7 | 5.3 | 7.4 | 7.4 | 8.6 |
| E | 40.0 | 35.3 | 33.6 | 30.6 | 29.7 | 27.7 | 27.2 | 26.0 |
| % Recovery | | | | | | | | |
| B | <0.5 | 3.4 | 5.4 | 6.0 | 12 | 17 | 17 | 20 |
| E | 91 | 80 | 76 | 70 | 68 | 63 | 62 | 59 |

EXAMPLE 7

Blocking of soluble ICAM-1 column

The primary reactants in the poly(ethylene) glycol reaction are the lysine residues on enlimomab. It is also possible that susceptible lysines in the sICAM-1 moiety coupled to the Emphaze matrix could become poly(ethylene) glycol-modified, thus rendering such molecules incapable of properly binding enlimomab. In order to minimize this potential problem a procedure for blocking of the lysine residues was developed. The following reagents have been used for such a blocking procedure including: DL-glyceraldehyde, sulfo-N-hydroxysuccinimide-acetate and succinic anhydride.

The sICAM-1-Emphaze column was prepared as described in Example 1. The column was further equilibrated with pH 6.0 formulation buffer (50 mM sodium phosphate, 100 mM NaCl). A solution of 500 mM DL-glyceraldehyde, 100 mM sodium cyanoborohydride in pH 6.0 formulation buffer was then prepared and vortex mixed for several minutes. Sodium cyanoborohydride, (157 mg), was then added and vortex mixed for approximately 30 seconds. The white solution, which still contains a considerable amount of unsolubilized glyceraldehyde, was placed on an end over end mixer and allowed to mix for an additional 15 minutes. Following this incubation the solution clarified. The few remaining insoluble white particles were removed by filtration of the solution through a 30 cc syringe fitted with 0.2 µm Gelman Acrodisc (25 mm) into a fresh container.

This blocking solution was then introduced onto the sICAM-1 Emphaze column (5 mL column volume) at a flow rate of 1.2 ml per minute. When 10 ml had been loaded and 15 ml remained in the load tube, the column outlet was placed into the load tube to close the loop. The solution was allowed to circulate for 2 hours at room temperature in this configuration.

After 2 hours, the outlet was removed to waste and the column washed with 5 volumes of pH 6.0 formulation buffer. At this point, the column is ready for use in preparing poly(ethylene) glycol-modified anti-ICAM-1. The capacity of the unblocked sICAM-1 column to bind enlimomab decreases with continued use. (FIG. 1) By using the aforementioned procedure, the capacity to bind enlimomab is greatly increased to over 20 cycles of the column.

EXAMPLE 8

Poly(ethylene) Glycol Modification of Another Anti-ICAM-1 antibody (RR1/1.1.1)

In order to demonstrate the generality of the above-described methods of poly(ethylene) glycol modification, such modification was attempted using an anti-ICAM-1 antibody other than enlimomab. The anti-ICAM-1 antibody designated RR/1.1.1 was therefore used in both the solution and column poly(ethylene) glycol-modification methods described in Example 1. The poly(ethylene glycol) utilized in these experiments was the SPA-5000 M.W. derivative. The solution and the column reactions were as described in Example 1. The results of this experiment are shown in Table 9.

TABLE 9

| RR1/1.1.1:PEG5000 Ratio | Reaction Time | pH | Average Degree of PEG Modification | Activity in sICAM-1 assay |
|---|---|---|---|---|
| Solution Method of forming PEG-Adducts | | | | |
| 1:1 | 1 hr | 6.0 | 1 | Not done |
| 1:1 | 1 hr | 7.5 | 1 | 78% |
| 1:1 | 1 hr | 8.0 | 2 | 58% |
| 1:1 | 1 hr | 8.5 | 3 | 56% |
| 1:1 | 24 hr | 7.5 | 2 | Not done |
| 1:2 | 24 hr | 7.5 | 4 | 31% |
| 1:3 | 24 hr | 7.5 | 6 | 21% |
| 1:4 | 24 hr | 7.5 | 6 | 0% |
| 1:2 | 4 hr | 7.5 | 4 | 28% |
| 1:2 | 24 hr | 7.5 | 4 | 36% |
| Column Method of forming PEG-Adducts | | | | |
| 1:1 | | 7.5 | 5 | 39% |

EXAMPLE 9

Ability of Poly(ethylene) Glycol-Modified Anti-ICAM-1 Antibody to Inhibit Lymphocyte Homotypic Aggregation The poly(ethylene) glycol-modification reactions of Example 1 yielded poly(ethylene) glycol-modified enlimomab derivatives that were capable of binding sICAM-1 as determined by ELISA. In vitro lymphocyte aggregation studies were undertaken to identify poly(ethylene) glycol-modified derivatives that had retained anti-ICAM-1 function as demonstrated by their ability to inhibit lymphocyte homotypic aggregation.

The JY B-cell line (Terhost, C. T. et al., Proc. Natl. Acad. Sci. USA 73:910 (1976)) which expresses both ICAM-1 and LFA-1 was used in this assay was maintained in complete medium consisting of RPMI 1640 medium (Sigma, St. Louis, Mo.) supplemented with 10% fetal bovine serum (FBS) and 50 µg/ml gentamycin. T cell blasts were cultured from cynomolgus and squirrel monkeys. Blood was collected in heparin and leukocytes were isolated by ficoll-hypaque gradient separation (Pharmacia, Sweden). Cells were cultured for 13 days in medium consisting of 10% FBS-RPMI 1640 supplemented with 50 µg/ml gentamycin.

Cultured cells were washed two times with RPMI 1640 and suspended to a concentration of $10^6$ cells/ml in RPMI 1640 with FBS. Added to flat bottomed 96 well microtiter plates (Costar #3596, Cambridge, Mass.) were 100 µl of appropriately diluted antibody or 100 µl of RPMI with FBS as a control followed by 100 µl of cells at a concentration of $10^6$ cells/ml in RPMI 1640 with FBS. In wells requiring activation, $2.7 \times 10^{-5}$ M phorbol 12-myristate 13-acetate (PMA) was added. This yielded a final concentration of $1.4 \times 10^{-5}$ PMA and $1 \times 10^5$ cells/well. The plates were incubated at 37° C. Plates containing JY cells were incubated for one hour while those containing monkey T cells were incubated for 4 hours. Aggregation was scored using a light microscope at 100× magnification. Scoring was done blindly in single wells. enlimomab was tested at final concentrations between 0.1 to 500 µg/ml. The degree of aggregation was scored between 0 and 5+. A score of zero indicated that essentially no cells were in clusters; 1+ indicated less than 10% of the cells were in aggregates; 2+ indicated that less than 50% of the cells were aggregated; 3+ indicated that up to 100% of the cells were in small, loose clusters; 4+ indicated that up to 100% of the cells were aggregated in larger clusters; and +5 indicated that 100% of the cells were in large, very compact aggregates.

Antibodies were functionally characterized for inhibition of homotypic aggregation mediated by LFA-1/ICAM-1 adhesion interactions by determining their respective $IC_{50}$ (i.e., the concentration at which 50% of aggregation is inhibited). The results of a comparison of native enlimomab and various poly(ethylene) glycol-modified derivatives is shown in Table 10.

TABLE 10

| Experimental Series I Solution-Based Modification | $IC_{50}$ µg/ml |
|---|---|
| Enlimomab | 0.2 |
| mg Enlimomab:mg PEG | |
| 1:1 | 0.2 |
| 1:2 | 3.0 |
| 1:3 | 1.5 |
| 1:4 | <0.1 |
| 10:1 | 0.4 |

| Experimental Series II Solution-Based Modification | $IC_{50}$ µg/ml |
|---|---|
| Enlimomab | 1.5 |
| mg Enlimomab:mg PEG | |
| 4:1 | 6.0 |
| 10:1 | 1.5 |
| 20:1 | 0.8 |
| 50:1 | 0.8 |
| 100:1 | 1.5 |

| Experimental Series III Solution-Based Modification | | $IC_{50}$ µg/ml |
|---|---|---|
| Enlimomab | | 0.1 |
| mg Enlimomab:mg PEG | Time | |
| 10:1 | 30 Min. | 0.8 |
| 10:1 | 1 Hour | 0.4 |
| 10:1 | 2 Hours | 0.4 |
| 20:1 | 30 Min. | 0.2 |
| 20:1 | 1 Hour | 0.4 |
| 20:1 | 2 Hour | 0.4 |
| 4:1 | 15 Min. | 3.0 |

TABLE 10-continued

| Experimental Series IV Column-Based Modification | $IC_{50}$ µg/ml |
|---|---|
| Enlimomab | 0.6 |
| BIRR10 | 0.2 |

As shown in Table 10, the $IC_{50}$ of BIRR10 in B-cell homotypic JY aggregation was about 0.2 µg/ml. The $IC_{50}$ of poly(ethylene) glycol-modified enlimomab was found to vary among the different poly(ethylene) glycol-modification processes. Several poly(ethylene) glycol-modified derivatives (including BIRR10) retained equivalent $IC_{50}$ to the native murine enlimomab.

Poly(ethylene) glycol-modified enlimomab derivatives were tested for the ability to bind to monkey T cell blasts and to thereby inhibit homotypic aggregation induced by PMA activation. Both 1924-11 (poly(ethylene) glycol-modified in solution) and BIRR10 (poly(ethylene) glycol-modified on the sICAM-1 column) inhibited aggregation of squirrel monkey T cell blasts as well as native enlimomab antibody at the concentration tested (10.0 µg/ml). Furthermore, BIRR10 inhibited aggregation of Cynomolgus monkey T cell blasts as well as the native enlimomab. (Table 11). Table 11 shows the degree of homotypic aggregation using 10 µg/ml of the indicated antibody. The solution poly(ethylene) glycol-modified enlimomab had an average of 2-3 PEG adducts. The column poly(ethylene) glycol-modified enlimomab had an average of 5 PEG adducts.

TABLE 11

| Antibody | PEG/ Antibody | Squirrel Monkey 1 | Squirrel Monkey 2 | Cynomolgus Monkey 1 | Cynomolgus Monkey 1 |
|---|---|---|---|---|---|
| No Antibody (Control) | — | 3.0+ | 3.0+ | 4.0+ | 4.0+ |
| Enlimomab | 0 | 1.0+ | 0.0+ | 2.0+ | 3.0+ |
| Solution PEG-Modified Enlimomab | 2-3 | 1.0+ | 1.0+ | 4.0+ | 4.0+ |
| Column PEG-Modified Enlimomab (BIRR10) | 5 | 0.5+ | 1.5+ | 3.0+ | 3.0+ |

EXAMPLE 10

FcR Binding Properties of poly(ethylene) glycol-modified Anti-ICAM-1 Antibody

Receptors specific for binding the Fc region of IgG ("FcR") are present on the surface of several types of cells in the immune system. High affinity FcR (FcRI, CD64) are present on macrophages and activated polymorphonuclear leukocytes (Anderson, C. L. et al., *Immunol. Today* 7:264 (1986); Lynch, R. G., et al.,. *Molec. Immunol.* 27:1167 (1990); Shen, L., et al., 1987. *J. Immunol.* 139:534 (1987)). Low affinity FcR (FcRII, CD32) are present on macrophages, B cells, and neutrophils (1, Petroni, K. C. et al., *J. Immunol.* 140:3467 (1988); Bentin, J. et al., *Cell Immunol.* 132:339 (1991)). Although aggregated and antigen-complexed IgG bind well to both types of FcR, different isotypes of human and mouse IgG bind FcRI and FcRII with different binding affinities (Rayetch, J. V. et al., *Annu. Rev. Immunol.* 9:457 (1991)). The primary functions of FcR appear to be in regulating immune responses, for example, internalization and degradation of immune complexes in macrophages and negative modulation of antibody responses in B cells (Ravetch, J. V. et al., *Annu. Rev. Immunol.* 9:457 (1991)).

Antibodies administered as therapeutic agents bind to FcR in vivo and present a unique situation to the immune system when the target antigen of the antibody is a molecule on the surface of monocytes or lymphocytes. If the monoclonal antigen specificity of a therapeutic antibody bound to FcR positive cells is directed against lymphocytes, cross-linking between the lymphocytes and FcR positive cells may result in cellular activation and adverse side effects (Krutmann, J. et al., *J. Immunol.* 145:1337 (1990); Thistlethwaite, J. R. et al., *Am. J. Kidney Dis.* 11:112 (1988)). Introduction of point mutations in the CH2 domain, the region that has been shown to bind FcRI and FcRII (Woof, J. M., et al., *Mol. Immunol.* 21:523 (1984); Duncan, A. R. et al., *Nature* 332:563 (1988)), was found to decrease the affinity of antibodies for FcR (Alegre, M.-L. et al., *J. Immunol.* 146:3461 (1992); Angal, S. et al., *Mol. Immunol.* 30:105 (1993)). These changes in FcR binding properties have been demonstrated to significantly decrease nonspecific effects of antibodies on cellular activation in vitro (Alegre, M.-L. et al., *J. Immunol.* 146:3461 (1992)) and also to change in vivo characteristics of antibodies (Angal, S. et al., *Mol. Immunol.* 30:105 (1993)). Thus, it is desirable to investigate the FcR binding properties of antibodies that are being evaluated as therapeutic agents.

FcR binding is typically measured in a rosetting assay (Fritsche, R. et al., *J. Immunol.* 121:471–478 (1978)). In rosetting assays, antibodies are coated onto fixed erythrocytes (E), and the ability of the coated E to bind FcRI and/or FcRII positive cells is measured by counting the number of rosette-forming cells (cells with 3 or more coated E bound). Antibodies coated on E are essentially aggregated and, although this can eliminate the ability to distinguish between FcRI and FcRII binding, the use of cell populations differentially expressing FcRI and FcRII as well as blocking antibodies to FcR makes it possible to assign Fc binding properties to FcRI or FcRII. In this study, a rosetting assay was used to compare the FcR binding properties of BIRR10 (the poly(ethylene) glycol-modified anti-ICAM-1 antibody) to those of the parent anti-ICAM antibody, enlimomab.

Thus, to measure FcR binding, cells were counted, washed once, and resuspended at $1 \times 10^7$/ml in RPMI 1640, 10% FCS. Rosetting tubes were set up as described (Yodoi, J. et al., *J. Immunol.* 122:2577 (1979)) in round-bottom polypropylene culture tubes and consisted of 6 µl FCS, 15 µl coated fixed ox erythrocytes ($E_o$) (2% solution), 15 µl RPMI-1640, 10 mM HEPES, pH 7.3, 15 µl HBSS, 15 µl cells at $1 \times 10^7$/ml ($1.5 \times 10^5$ cells). F(ab')$_2$ of enlimomab were included at a final concentration of 50 µg/ml in each tube to prevent nonspecific binding of Eo sensitized with anti-ICAM-1 to ICAM-1 on the surface of lymphocytes/ monocytes used as indicator cells. In some samples 15 µl anti-FcRI (0.1 mg/ml) was added instead of the HBSS and preincubated for 10 minutes with cells before the addition of sensitized $E_o$. After addition of all components, tubes were briefly vortexed at low speed, incubated for 10 minutes at 37° C., vortexed briefly at low speed, centrifuged 7 minutes at 700 rpm (GS-6KR centrifuge, Beckman), placed on ice and incubated overnight in the cold.

For red blood cell coating, ox blood was obtained from the Colorado Serum Co., Denver, Colo. Erythrocytes were fixed and stored as an 8% solution in D-PBS as described (Fritsche, R. et al., *J. Immunol.* 121:471–478 (1978)). Fixed ox erythrocytes ($E_o$) were washed once in freshly prepared 0.1M sodium acetate, pH 5.0 (acetate buffer) and resuspended to 4% solution in acetate buffer. To coat $E_o$, 250 µl washed $E_o$ in acetate buffer were added to 250 µl protein solution (100 µg in equal volumes acetate buffer and borate buffered saline (BBS))in a round-bottom polypropylene vial and rotated 2 h at room temperature. Sensitized $E_o$ were washed 3 times in cold Hank's balanced salt solution (HBSS) and resuspended to a final concentration of 2% in HBSS (Fritsche, R. et al., *J. Immunol.* 121:471–478 (1978)).

For counting rosettes dye solution was freshly prepared and consisted of 0.4 ml HBSS, 0.1 ml FCS, 0.25 ml 0.2% toluidine blue in D-PBS. To count, a rosetted sample was removed from the ice and rolled between two hands 17 times, 20 µl was removed and added to 9.2 µl dye solution in round-bottom culture tubes, samples mixed 3 times with the pipette tip and transferred to a hemocytometer. After cells settled, at least 300 total lymphocytes/monocytes (blue) were counted and rosettes were scored as the presence of at least 3 attached $E_o$. Clumps were ignored. The percentage rosetted cells of the total cells counted was calculated (Angal, S. et al., *Mol. Immunol.* 30:10513 (1993)).

In a first experiment, CD19$^+$ cells (B cells) and CD14$^+$ cells (monocytes) were isolated from peripheral blood mononuclear cells. Peripheral blood was collected from 2 or 3 donors by venipuncture into heparin coated vacutainers. Peripheral blood mononuclear cells were isolated by gradient sedimentation using Ficoll-Paque (Pharmacia) according to the manufacturer's instructions. CD19$^+$ cells were isolated using a Dynabead cell separation procedure according to the manufacturer's instructions (Dynal). Peripheral blood mononuclear cells were incubated with Dynabeads M-450 Pan-B (anti-CD19 coated magnetic beads), isolated using the Dynal MPC magnet, washed, and released from the Dynabeads using DETACH a BEAD-19 antiserum according to the manufacturer's instructions. CD14$^+$ cells were isolated using anti-CD14 coated magnetic beads (AMAC) as described by the manufacturer. CD19$^-$, CD3-depleted cells were isolated as the nonmagnetic fraction using cells that did not bind to Dynabeads M-450 Pan-B (anti-CD19) above using AMAC magnetic separation products according to the manufacturer's instructions. AMAC IObeads-anti mouse IgG were coated with anti-CD3 (AMAC). CD19$^-$ cells were incubated with the anti-CD3 coated beads and the CD3$^+$ cells removed. Two rounds of negative selection were performed to give CD19$^-$ CD3-depleted cells.

Cells were washed once in cold FACS buffer (Dulbecco's phosphate buffered saline (D-PBS), 2% BSA, 0.2% sodium azide), resuspended in 50 µl FACS buffer for each sample ($1.0–0.5 \times 10^5$ cells/sample), and plated in a well of a "V"-bottom 96-well polystyrene plate (Dynatech Laboratories, 001-010-2701). All staining procedures were carried out on ice. First step antibodies were added in 100 µl FACS buffer as described below. Cells were mixed with a multichannel pipette and incubated on ice for 1 hour.

Anti-FcRI (CD64) (clone 10.1, mouse IgG1) was purchased from Research Diagnostics, Inc. (RDI-CBL491) and used at a final concentration of 10 µg/ml. Antibody-containing culture supernatant was used at a final dilution of 1:2. Anti-FcRIII (CD16) (clone CLB-149, mouse IgG2a) was purchased from Research Diagnostics, Inc. (CLB-CD16, lot #1389-04-01) and used at a final concentration of 10 µg/ml. Antibody enlimomab (mouse IgG2a) was used from a 5 mg/ml stock solution at a final concentration of 20 µg/ml. Antibody RPC-5 (mouse IgG2a) was purchased from Cappel (Organon Teknika Corp.) and used as an isotype control antibody at a final concentration of 20 µg/ml. Cells producing U7.6 antibody (mouse IgG1 anti-TNP) was grown in serum free medium and purified as described by Hardy, R. R. (In: *Handbook of Experimental Immunology*. D. M. Weir, ed. Blackwell Scientific Publications, Cambridge, Mass., p. 13. (1986)). U7.6 was used as an isotype control antibody at a final concentration of 10 µg/ml.

There were insufficient numbers of $CD19^+$ cells for surface phenotype analysis. Staining the peripheral blood mononuclear cells for surface markers showed that, as expected, the lymphocyte population was $FcRI^-$, $FcRII^+$ (Table 12). The $CD14^+$ cells reaggregated with the anti-CD14 magnetic beads after staining and were filtered before analysis.

Flow cytometry was used to analyze the cell populations. Cells were washed by underlaying each sample with 50 µl filtered (0.2 µm) fetal calf serum (FCS) and centrifuging the plate for 6 minutes at 1600 rpm (GS-6KR centrifuge, Beckman). Supernatant medium was removed by aspirating and the second step staining reagent, R-phycoerythrin conjugated affinity purified goat F(ab')$_2$ anti-mouse IgG, human IgG absorbed (TAGO, 4950 (Biosource International)), was added in 100 µl FACS buffer (1/100 dilution). Cells were resuspended with a multichannel pipette and incubated on ice in the dark for 1 hour.

Cells were washed by underlaying each sample with 50 µl filtered FCS and centrifuging the plate for 6 minutes at 1600 rpm. After aspirating supernatant medium, cells were washed once in D-PBS, 0.2% sodium azide and fixed in D-PBS, 1% paraformaldehyde (0.5 ml). Samples were stored at 4° C. in the dark prior to flow cytometry analysis (FACSCAN, Beckton-Dickenson).

The flow cytometry analysis showed that the population remaining were primarily lymphocytes negative for FcRI and FcRII. This is consistent with these cells being T lymphocytes and with the low percentage of rosetted cells (see below). Flow cytometry analysis of the unseparated peripheral blood mononuclear cell population showed that the monocyte population was clearly $FcRI^+$ and $FcRII^+$, as expected (Table 12). In Table 12, data reported are for surface phenotype of stained unseparated peripheral blood mononuclear cells analyzed as two populations by forward and side scatter (lymphocytes and monocytes); legend: –, all cells were negative for surface marker; +, all cells were weakly positive for surface marker; ++, all cells were strongly positive for surface marker. When a portion of the cell population was positive, that percentage is given. FcRIII positive lymphocytes were present as two populations, expressing low and high levels of FcRIII. The percentage reflects both positive populations together.

TABLE 12

| Surface | Experiment 1 | | Experiment 2 | |
| --- | --- | --- | --- | --- |
| Marker | Lymphocytes | Monocytes | Lymphocytes | Monocytes |
| FcRI | – | ++ | – | ++ |
| FcRII | 13% ++ | + | 12.5% ++ | + |
| FcRIII | 13% + | 13% + | 20% + | 15% + |
| ICAM-1 | + | + | + | ++ |

The results suggest BIRR10 exhibits decreased binding to both FcRI and FcRII as compared to enlimomab.

The percentage of rosettes formed by the "CD14+" cells was low, since the cells in this population that could be analyzed were lymphocytes. In support of the similar phenotypic analysis of the $CD19^+$ and $CD14^+$ populations, the rosetting results on the two populations were similar. $E_o$ coated with enlimomab, chimeric IgG1, mouse IgG2a, human IgG1, or human IgG4 formed similar percentages of rosettes (47.5%±4.9). Background rosetting by GSA-coated $E_o$ was 23.9%. $E_o$ coated with poly(ethylene) glycol-modified anti-ICAM-1 (BIRR10) formed significantly lower percentages of rosettes (29.2% and 35.6%, respectively) than the other $E_o$ tested.

In a second experiment, $CD19^+$ cells (B cells) and CD19–, CD3-depleted cells (monocytes) were isolated from peripheral blood mononuclear cells. There were insufficient numbers of $CD19^+$ cells for surface phenotype analysis. Staining the peripheral blood mononuclear cells for surface markers showed that, again, the lymphocyte population was $FcRI^-$, $FcRII^+$ (Table 12). The CD19–, CD3-depleted cells were 42% monocytes as compared to 31% monocytes in the unseparated peripheral blood mononuclear cell population. Thus the enrichment of monocytes by magnetic bead depletion of $CD19^+$ and $CD3^+$ cells was not efficient. Flow cytometry analysis of the unseparated peripheral blood mononuclear cell population again showed that the monocyte population was clearly $FcRI^+$ and FcRII+, as expected (Table 12).

The binding of CD19+ and CD19–, CD3-depleted cells to $E_o$ gave results that were similar to those obtained in the first experiment. $E_o$ coated with poly(ethylene) glycol-modified anti-ICAM-1 antibody (BIRR10) formed lower percentages of rosettes (25.3% and 21.3%, respectively) than the other $E_o$ tested on CD19+ cells (31.7%±3.1). Although the CD19–, CD3-depleted cells were enriched for monocytes and the population was more similar to unseparated peripheral blood mononuclear cells, the rosetting results were similar to those on the CD19+ cells. With the exception of the irrelevant IgG4, $E_o$ coated with poly(ethylene) glycol-modified anti-ICAM-1 (BIRR10) formed lower percentages of rosettes (25.5% and 21.6%, respectively) than the other $E_o$ tested on CD19–, CD3-depleted cells (35.6%±2.2). When anti-FcRI was included in the rosetting assay with chimeric IgG1, the percentage of rosettes formed was decreased (24.2% and 25.0%, respectively) to the level found with BIRR10. This indicated that rosettes formed by CD19–, CD3-depleted cells predominantly reflected the binding of antibody-coated $E_o$ to FcRI.

The above-described results indicated that a poly (ethylene) glycol-modified anti-ICAM-1 antibody (BIRR10) coated on fixed ox erythrocytes exhibited decreased binding to $CD19^+$ (B) cells relative to enlimomab and chimeric IgG1. In the first experiment, the conclusion from the phenotypic analysis would be that this reflects decreased binding to FcRII.

The poly(ethylene) glycol-modified anti-ICAM-1 antibody (BIRR10) coated on fixed ox erythrocytes also exhibited decreased binding to CD19–, CD3-depleted cells (monocyte-enriched). Binding of chimeric IgG1 was decreased significantly by preincubating the CD19–, CD3-depleted cells with anti-FcRI. This indicated that in the second experiment, the decreased binding of BIRR10-coated ox erythrocytes to CD19–, CD3-depleted cells reflected deceased binding to FcRI. These results are consistent with the inability to distinguish binding to FcRII in the presence of the high affinity FcRI when using aggregated IgG (coated erythrocytes). It would be expected that under the rosetting conditions used that FcRI binding would dominate. The results indicate that attachment of PEG to BIRR10 decreased FcR binding.

EXAMPLE 11

Rabbit Immunogenicity Studies

To test the different poly(ethylene) glycol-modification processes, rabbit immunogenicity experiments were conducted. The tests were designed to evaluate the immunogenicity of the enlimomab molecule and its derivatives using a dosage regimen and route of administration that was likely to produce an immune response.

Four New Zealand white rabbits of either sex from currently-approved SPF vendor(s) were used per antigen, in accordance with ACUC Standard Method #91-01-D. Acepromazine, an anesthesia was administered (1 mg/kg) subcutaneously 20 minutes prior to serum collection. Rabbits were sensitized to murine antibody by weekly injections of 1 mg/kg of sterile antibody formulation (as per protein concentration)intraperitoneally or intravenously for four weeks. Blood was collected from the central ear artery prior to each injection of antibody and two weeks after the last immunization.

An ELISA was used for the detection of anti-murine antibodies in rabbit serum. Serum was prepared from rabbit blood by centrifugation within one hour after blood collection. The sera was aliquoted and frozen at −70° C. until use. The sensitizing native murine antibody was coated onto 96 well Linbro E.I.A. plates by pipetting 50 µl of antibody at a concentration of 10 µg/ml (diluted in Dulbecco's phosphate buffered saline −Dpbs) into the appropriate wells. The plates were incubated for one hour at room temperature. The wells were washed 3 times with 200 µls of Dpbs. The wells were blocked with 2% bovine serum albumin in Dpbs (bsa-Dpbs) (200 µls/well) overnight at 4° C. The block was removed immediately prior to addition of the serum titration (diluted in 1% bsa-Dpbs) (50 µl/well). Usually, twelve two-fold dilutions for each bleed (starting at 1/500) were used to determine the rabbit titer. The sera titration was incubated for 2 hours at 37° C. The wells were washed 3 times with 200 µl of Dpbs. The detecting antibody, Goat F(ab)'$_2$ anti-rabbit Ig (H&L)-horse radish peroxidase conjugate (Tago) was added at 1/1800 (diluted in 1% bsa-Dpbs) 50 µl/well. The wells were incubated for 1 hour at 37° C. The wells were washed 3 times with Dpbs (200 µl/well). The wells were washed once with 50 µls of ABTS substrate buffer. 50 µls of ABTS substrate (Zymed) is added. Color was read on a Molecular Devices Vmax ELISA reader at 405 nm. The endpoint was determined by the control antibody (Rabbit anti-mouse IgG at 1 µg/ml) reaching an OD reading of approximately 1.000. To compare between rabbits, time points, and antibody formulations the sera titration with a reading of approximately 0.5 OD was used. 17 enlimomab derivatives were characterized. Enlimomab elicited an immune response in all rabbits in all studies. Three derivatives were identified that produced a marked decrease in immunogenicity while retaining sufficient (>20% of the native mouse antibody) ICAM-1 binding capabilities to permit their use as a human therapeutic.

Figure 2:
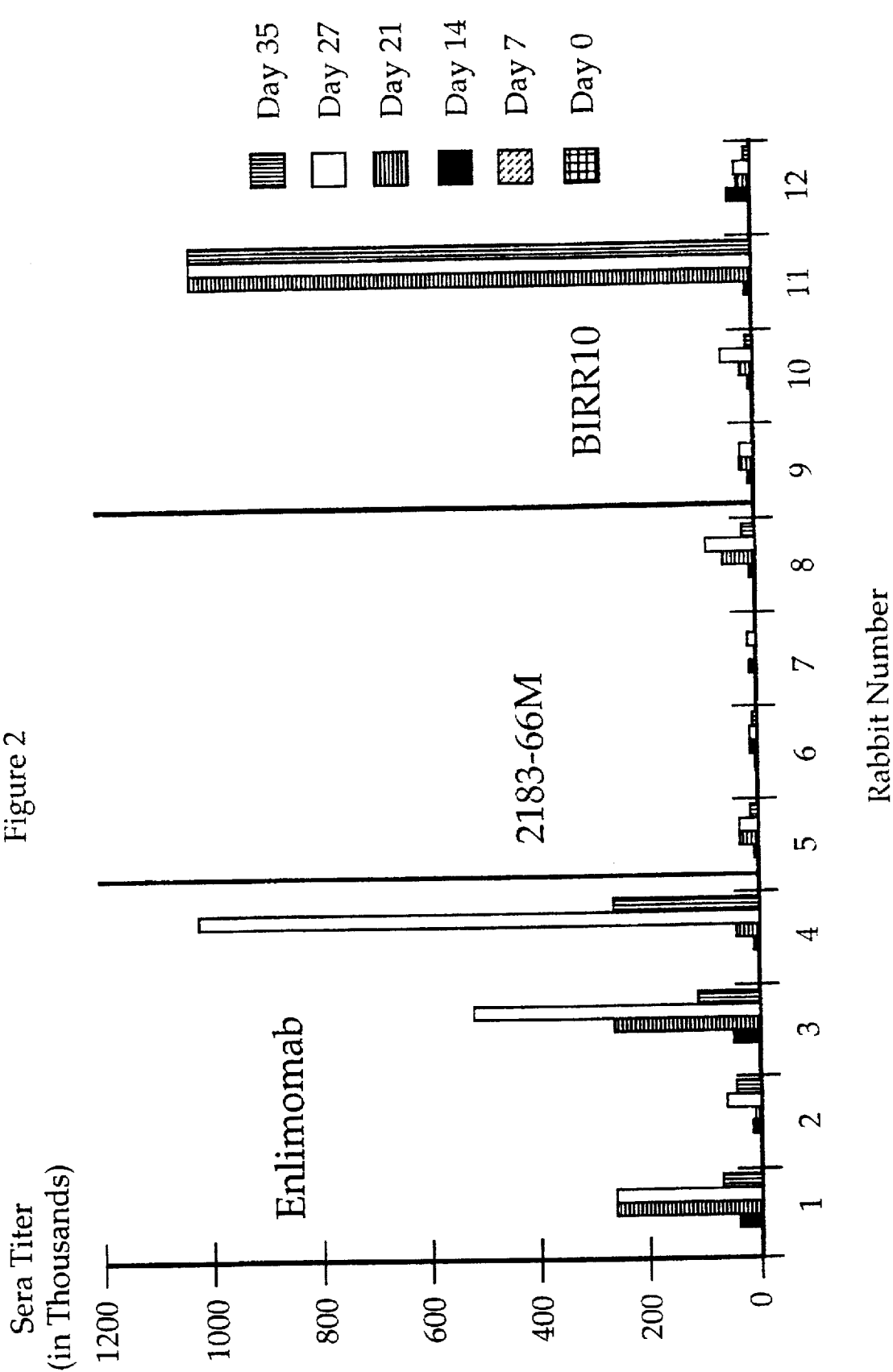
FIG. 2 shows the anti-enlimomab sera titer (in thousands) of individual rabbits after intraperitoneal injection of either enlimomab, PEG-enlimomab antibody 2183-66M, or PEG-enlimomab antibody BIRR10.

FIG. 2 shows the anti-enlimomab sera titer (in thousands) of individual rabbits after intraperitoneal injection of either enlimomab, antibody 2183-66M (a PEG-enlimomab derivative having an average of 5 PEG adducts per antibody molecule that was obtained using a CA3 anti-idiotypic column), or BIRR10 (a PEG-enlimomab derivative having an average of 5 PEG adducts per antibody molecule that was otained using an sICAM-1 column). The Figure demonstrates that the PEG-modified enlimomab had substantially lower immunogenicity than the native antibody.

Figure 3:
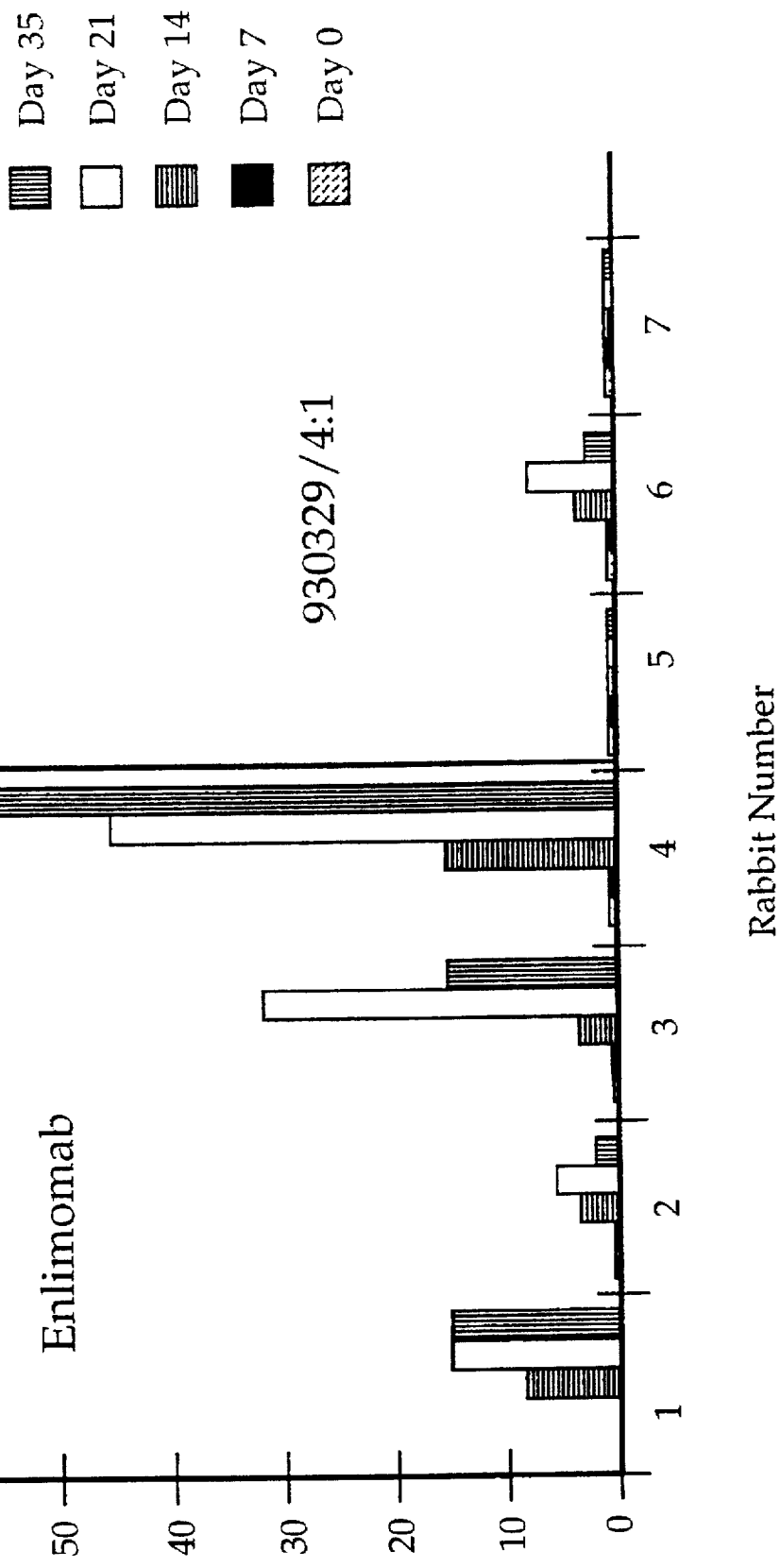
FIG. 3 shows the anti-enlimomab sera titer (in thousands) of individual rabbits after intraperitoneal injection of either enlimomab or PEG-enlomomab antibody 930329/4:1.

FIG. 3 shows the anti-enlimomab sera titer (in thousands) of individual rabbits after intraperitoneal injection of either enlimomab or antibody 930329/4:1 (a PEG-enlimomab derivative having an average of 3 PEG adducts per antibody molecule). This Figure also demonstrates that the PEG-modified enlimomab had substantially lower immunogenicity than the native antibody.

Figure 4:
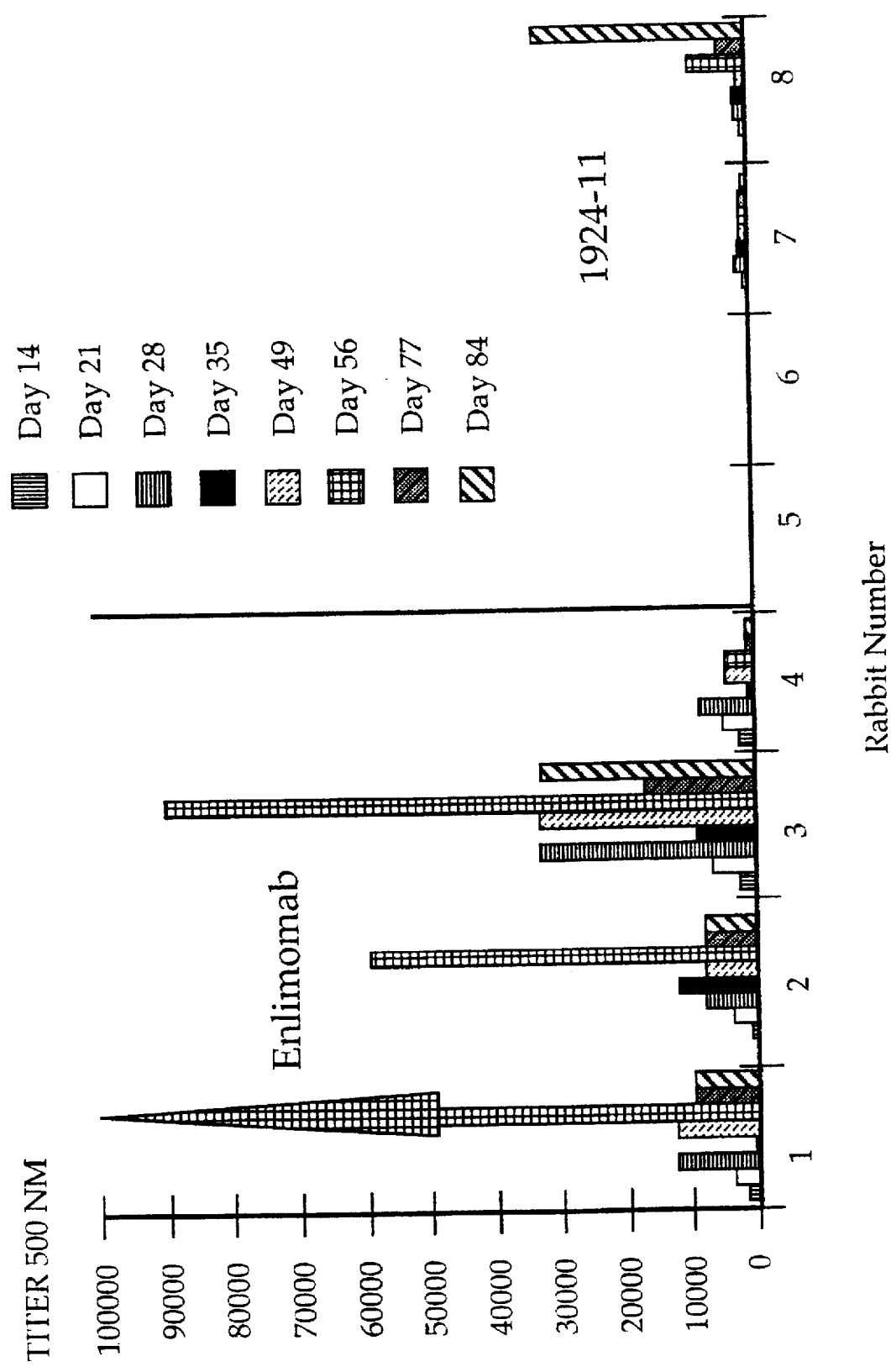
FIG. 4 shows the anti-enlimomab sera titer (in thousands) of individual rabbits after intravenous injection of either enlimomab or PEG-enlomomab antibody 1924-11.

FIG. 4 shows the anti-enlimomab sera titer (in thousands) of individual rabbits after intravenous injection of either enlimomab or antibody 1924-11 (a PEG-enlimomab derivative having an average of 2 PEG adducts per antibody molecule). As indicated in the Figure the PEG-modified enlimomab had substantially lower immunogenicity than the native antibody.

Two derivatives were prepared on a solid support, thereby protecting the binding site of enlimomab. Derivative 2183-66M, prepared from the CA3 ICAM-1 anti-idiotypic column, reduced the immunogenicity significantly. After 4 doses of 1 mg/kg of antibody intraperitoneally (IP), the mean log sera titer was reduced from 5.55 (anti-enlimomab activity) to 4.50 (anti-2183-66M activity) which was statistically significant by t-test analysis. (Table 13). This reduction reflected a 10-fold decrease of the immune reaction to murine antibody. Another enlimomab derivative, P0045, was prepared from a sICAM-1 column. After 4 doses of 1 mg/kg IP the mean log sera titer was reduced from 5.55 (anti-enlimomab activity) to 4.88 (anti-sICAM-1 activity). This reduction was not statistically significant by t-test analysis (Table 13). In Table 13, "SEM" refers to the standard error of the mean.

TABLE 13

| Compound | Sera Titers at Day 27 | | | | |
|---|---|---|---|---|---|
| | Mean | Std Dev | SEM | T | P value |
| Enlimomab | 5.55 | 0.627 | 0.313 | | |
| PEG-Enlimomab (made on CA3 anti-idiotypic column) | 4.50 | 0.549 | 0.274 | 2.528 | 0.045 |
| PEG-Enlimomab BIRR10 (column method PEG-enlimomab) | 4.88 | 0.995 | 0.497 | 1.151 | 0.293 |
| Enlimomab | 4.12 | 0.620 | 0.310 | | |
| PEG-Enlimomab BIRR10 (solution method PEG-enlimomab) | 3.11 | 0.488 | 0.244 | 2.558 | 0.043 |

The third derivative identified as effective in reducing immunogenicity was prepared in solution. The derivative was administered IP, 1 mg/kg, 4 doses. The mean log sera titer was reduced from 4.12 (anti-enlimomab activity) to 3.11 (anti-930 activity) which was statistically significant by t-test (Table 13) reflecting a 10 fold decrease in the immune response. This derivative was further tested by intravenous (IV) administration. The immunization schedule consisted of 4 weekly injections of 1 mg/kg IV followed by monthly injections of 1 mg/kg IV Sera samples were collected 7 days after each IV administration. There was a statistically significant reduction of the immune response following the 4 weekly doses from a mean log titer of 4.09 (anti-enlimomab activity) to 3.04 (anti-1924-11 activity). After the subsequent monthly dose (by intravenous injection) the mean log titer of anti-enlimomab activity increased to 4.77 and the mean log titer of the poly(ethylene) glycol-modified anti-1924-11 derivative did not increase (3.07) (Table 14). Notably, 2 of the 4 rabbits did not mount an immune response measurable by ELISA. The data is shown in FIG. 5.

TABLE 14

| Compound | Sera Titers at Day 28 and 56 | | | | |
|---|---|---|---|---|---|
| | Mean | Std Dev | SEM | T | P value |
| | Day 28 | | | | |
| Enlimomab | 4.09 | 0.284 | 0.142 | | |
| PEG-Enlimomab (solution method) | 3.04 | 0.404 | 0.202 | 4.26 | 0.005 |
| | Day 56 | | | | |
| Enlimomab | 4.77 | 0.874 | 0.437 | | |
| PEG-Enlimomab (solution method) | 3.07 | 0.569 | 0.284 | 3.25 | 0.017 |

The rabbit immunogenicity experiments described above demonstrate that the poly(ethylene) glycol-modification of enlimomab modulates the immunogenicity of the murine antibody. Furthermore, in vitro binding studies and in vivo inflammation experiments show that the specificity of enlimomab is retained after poly(ethylene) glycol-modification. In our studies of 17 poly(ethylene) glycol-modified enlimomab derivatives, three derivatives were identified as functional products (in vitro)which markedly reduced immunogenicity (in vivo). The ICAM-1 binding capacities were approximately the same for each derivative (equivalent to the binding of enlimomab Fab fragments). All three derivatives, when administered intraperitoneally, reduced immunogenicity by 10 fold. There was not a statistical difference between the different poly(ethylene) glycol-modification derivatives in the capacity to reduce immunogenicity. Of note was the observation of a variable immune response to enlimomab by different animals in these experiments. Although this variability may be predictive of the responses generated in other species and in humans receiving enlimomab, an immune response was generated in every rabbit that received enlimomab. Similarly, rabbits receiving poly(ethylene) glycol-modified enlimomab also produced a variable response to the modified antibody, however, some animals did not produce a detectable immune response (measurable by ELISA) while others had a greatly reduced reaction. These data indicate that by poly(ethylene) glycol-modification of the enlimomab antibody, one may re-treat patients with anti-ICAM-1 therapy as may be required for chronic inflammatory disease without inducing a biologically significant human anti-mouse antibody (HAMA) response.

In sum, enlimomab when administered at 1 mg/kg either IP or IV produced an immune response in all rabbits. Three poly(ethylene) glycol-modified derivatives (one made in solution phase), one made on an sICAM-1 column and one made on a CA3 column) reduced immunogenicity by 10 fold when repeatedly administered (4 doses) at 1 mg/kg IP. Furthermore, when derivative 1924-11 was administered by an IV route, 2 of 4 rabbits did not respond to 6 doses of poly(ethylene) glycol-modified antibody while the remaining two rabbits had a minimal response.

EXAMPLE 12

FcR-Induced Oxidative Burst Analysis of poly (ethylene) glycol-modified Anti-ICAM-1 Antibody The therapeutic use of murine monoclonal antibodies has been complicated by inflammatory responses induced by the Fc portion of the antibody binding to Fc receptor (FcR) on the cell surface. In addition to the accelerated clearance of the therapeutic antibody from the circulation, several important biological functions triggered by Fc-FcR interactions. These functions, initiated through the crosslinking of the FcR, include phagocytosis, superoxide generation, mediator release (IL1, IL6, TNF-alpha, etc.), regulation of Ig production and enhanced antigen presentation (van de Winkel, Jan. G. J., et al., Immunology Today, 14:215–221 (1993)). Fc$\gamma$RI (CD 64) binds monomeric IgG and is constitutively expressed on monocytes and may be induced on neutrophils. The Fc$\gamma$RII (CD32) is constitutively expressed on monocytes, granulocytes, and B cells binds human antibody in its multimeric forms (as seen with immune complexes) and will also bind to multimeric murine IgG2a antibodies.

Enlimomab, a murine IgG$_{2a}$, will bind to human leukocytes via the Fc$\gamma\gamma$RI on PBMC and F$\gamma$RII on neutrophils. To test the effects of the different poly(ethylene) glycol-modification processes on the Fc portion of the enlimomab molecule, oxidative burst studies were conducted. These studies were designed to detect cellular activation through Fc-FcR interactions. Elimination of the FcR binding capacity through poly(ethylene) glycol-modification (as demonstrated by an attenuated oxidative burst) would be beneficial in that anti-ICAM-1 mAb would not be cleared as quickly from the circulation and undesired biological effects would be ameliorated.

Polystyene tubes (Exoxemis, San Antonio, Tex.) were coated with 100 µl of purified soluble ICAM-1, diluted in Dulbecco's PBS ("Dpbs," Gibco, Grand Island, N.Y.), at a concentration of 10 µg/ml for four hours at room temperature. The tubes were washed twice with Dpbs. The tubes were blocked overnight with 250 µl of 2% bovine serum albumin-Dpbs at 4° C. The tubes were emptied and 100 µl of the appropriate antibody was added at a concentration of 50 µg/ml diluted in 1% bsa-Dpbs for 1 hour at 37° C. The tubes were washed twice with Dpbs immediately before use. This procedure was used to orient the mAb so that the Fc portion of the antibody was available to engage with FcR receptors on the leukocytes while the antibody binding sites were inactivated by the ligand attached to the solid substrate. Human peripheral blood was collected in heparin. The neutrophils and PBMC were isolated using Dextran sedimentation followed by Ficoll-Paque (Pharmacia, Uppsala, Sweden) gradient separation as per manufacturer's instructions.

For oxidative burst experiments, cells were washed three times and resuspended at $3 \times 10^6$ cells/ml in Dulbecco's PBS (Gibco, Grand Island, N.Y.). The 600 µl of luminol balanced salt solution (Exoxemis, San Antonio, Tex.) was added to each tube followed by 100 µl of FMLP. The final volume was 800 µls with the FMLP final concentration of $1 \times 10^{-7}$M. 100 µl of purified cells was added to each tube (in triplicate) at a concentration of $3 \times 10^6$ cells/ml immediately before measurement of the oxidative burst. The FMLP concentration of $10^{-7}$M was selected because alone it did not stimulate an oxidative burst from PBMC but did prime the PBMC thereby enhancing the oxidate burst generated by receptor engagement. Any components omitted in control samples were replaced with an equivalent volume of the respective buffer. Samples were read in a Berthold AutoLumat LB953 luminometer (Wildbad, Germany) at 37° C. for 90 minutes. Time course curves were generated and the integral area under the curve was calculated with software from Berthold.

The results of this experiment demonstrated that enlimomab induced an oxidative burst alone ($3.7 \times 10^7$ chemiluminescence integral) or an enhanced burst with a suboptimal priming stimulus of the bacterial peptide FMLP ($4.7 \times 10^7$ chemiluminescence integral).

The poly(ethylene) glycol-modification of the enlimomab antibody modulated the oxidative burst induced by Fc-FcR binding interactions on both neutrophils and PBMC (Table 15). The poly(ethylene) glycol-modification reduced the oxidative burst on unstimulated PBMC to almost baseline values ($3.0 \times 10^7$ chemiluminescence integral) reflecting an inhibition of triggering through the FcγRI on the monocyte. Furthermore, poly(ethylene) glycol-modification of enlimomab also completely inhibited the oxidative burst on unstimulated neutrophils ($1.8 \times 10^7$ chemiluminescence integral) reflecting on inhibition of triggering through the FcγRII on the neutrophil. Poly(ethylene) glycol-modification of enlimomab also reduced the augmented oxidative burst of FMLP-stimulated PBMC and neutrophils to baseline levels ($4.1 \times 10^7$ and $6.9 \times 10^7$ chemiluminescence integral, respectively).

TABLE 15

Fc-FcR Induced Oxidative Burst
Chemiluminecence: Integral of $10^7$

| mAb Treatment | No FMLP | | FMLP | |
|---|---|---|---|---|
| | Expt. I | Expt. II | Expt. I | Expt. II |
| PMBC | | | | |
| No mAb | 2.8 | 1.5 | 3.3 | 3.3 |
| Enlimomab | 3.7 | 2.2 | 4.7 | 4.9 |
| 2-PEG-Enlimomab | 3.0 | 2.4 | 4.1 | 3.0 |
| 5-PEG-Enlimomab (BIRR10) | 3.2 | 2.4 | 4.0 | 3.3 |
| Granulocytes | | | | |
| No mAb | 1.8 | 3.1 | 7.2 | 27.0 |
| Enlimomab | 2.4 | 0.9 | 10.5 | 17.6 |
| 2-PEG-Enlimomab | 1.8 | 1.2 | 6.9 | 9.6 |
| 5-PEG-Enlimomab (BIRR10) | 2.0 | 1.3 | 5.3 | 7.4 |

The oxidative burst experiments described above demonstrated that the poly(ethylene) glycol-modification of enlimomab modulated the cellular activation components of the Fc structure. The native murine anti-ICAM-1 antibody enlimomab has been shown to induce an oxidative burst in both human PBMC and neutrophils through the interaction with FcγRI and FcγRII on the cell surface. Poly(ethylene) glycol-modification of the enlimomab antibody effectively reduced the capacity for the antibody to induce this Fc-FcR induced oxidative response. Two poly(ethylene) glycol-modified enlimompb derivatives (that were identified as functional products in vitro and showed reduced immunogenicity in rabbits) exhibited markedly reduced Fc-FcR induced oxidative burst on human leukocytes. These derivatives reduced the oxidative burst induced the FcγRI on human PBMC as well as the FcγRII on human neutrophils to baseline values. Furthermore, both PBMC and neutrophils that were primed with FMLP and then exposed to poly(ethylene) glycol-modified enlimomab did not produce an oxidative burst as compared to the augmented oxidative burst induced by native enlimomab. These data indicated that by poly (ethylene) glycol-modification of the enlimomab antibody, Fc-FcR interactions are eliminated and therefore poly (ethylene) glycol-modified anti-ICAM. The inhibition of Fc-FcR interaction is a significant step forward in reducing the unwanted effects and immunogenicity of the murine antibody. Poly(ethylene) glycol-modification may prolong the half life of enlimomab in vivo thereby making the initial treatment of anti-ICAM-1 therapy more effective. In addition, poly(ethylene) glycol-modification reduces immunogenicity and allows the readministration of poly(ethylene) glycol-modified enlimomab in a clinical application in chronic inflammatory disease.

In sum, poly(ethylene) glycol-modification processes performed in solution as well as those performed on soluble ICAM-1 solid supports eliminated the oxidative burst indicating that the ability of the Fc portion of enlimomab was modified so that it could no longer interact with the FcR's of the leukocytes and therefore the undesirable biological effects were ameliorated.

EXAMPLE 13

Monkey Inflammation Experiments

BIRR10 was compared to enlimomab ("enlimomab") for its ability to inhibit localized inflammation in squirrel monkeys (Saimiri Sciureus). Intradermal (ID) injection of inflammatory mediators in multiple sites on the backs of animals allowed comparison to control sites on the same animal. Measurement of radioactivity at skin sites after injection of a radioactive protein provided quantitation of vascular permeability at the injection sites.

In this study ID injections of 10 μg of bacterial lipopolysaccharide (S. typhosa, LPS) or saline were given. Twenty-four hours later animals were treated with either BIRR10 or enlimomab by intravenous (IV) injection. A separate group of animals were untreated controls. After antibody administration, second intradermal injections of saline, or of 100 μg of zymosan were given such that there were sites with saline/saline, saline/zymosan, LPS/saline and LPS/zymosan injections. Thirty minutes later each animal was given 20 μCi of $^{125}$I-labeled bovine serum albumin (BSA) by IV injection. Five hours later a blood sample was drawn, the animals were sacrificed, and the skin of the back removed. Injection sites were cut out by 8 mm diameter biopsy punch and their radioactivity measured. Aliquots of plasma were made and $^{125}$I activity measured so that skin radioactivity was converted to μl of plasma equivalents. To normalize for animal variations in skin thickness and batch to batch variations in the BSA, the permeability is expressed as the fold increase over saline injected sites. The results are shown in Table 16 ("n" denotes the number of experiments; Dose is in mg/kg; Data for BIRR10 with zymosan at 30 or 100 μg, and for enlimomab with zymosan at 100 μg have a $P<0.01$ as compared to control (mouse IgG2a) group; data for enlimomab with LPS and zymosan has a $P<0.05$ relative to the control group.

TABLE 16

| Treatment | Dose | n | LSP/Saline | Zymosan (30 μg) | Zymosan (100 μg) | LPS/ Zymosan |
|---|---|---|---|---|---|---|
| Mouse IgG | 3 | 4 | 1.40 ± 0.05 | 2.06 ± 0.19 | 3.72 ± 0.45 | 4.07 ± 0.57 |
| enlimomab | 3 | 3 | 1.44 ± 0.05 | 1.36 (n = 2) | 1.61 ± 0.11 | 2.32 ± 0.30 |
| BIRR10 | 3 | 6 | 1.52 ± 0.31 | 1.26 ± 0.07 | 1.51 ± 0.19 | 2.17 ± 0.32 |

As indicated in Table 16, there was no inhibition of the slight LPS-induced increase in vascular permeability by either of the antibodies at the doses tested. Sites that were injected with 30 and 100 μg zymosan the day of the study had 2 and 3.7 times more plasma, respectively, than the control sites. Enlimomab and BIRR10 inhibited the increase in vascular permeability induced by 100 μg zymosan by 57±3% and 59±5%, respectively. BIRR10 inhibited the increase in permeability induced by 30 μg zymosan by 39±3%. Enlimomab also seemed to inhibit this effect, however, because only two animals treated with enlimomab were tested with the 30 μg dose of zymosan this was not statistically significant. Enlimomab and BIRR10 also inhibited the increase in permeability at sites pretreated with LPS then stimulated with zymosan by 43±7% and 47±7%, respectively Histological examination of tissue from untreated animals revealed the presence of granulocytes in LPS and zymosan treated areas but not in the saline/saline control sites. LPS causes ICAM-1 up-regulation in vitro recruits leukocytes to the skin of primates and increases ICAM-1 expression in squirrel monkey skin vessels (as measured by enlimomab immunohistochemistry). Zymosan is a cell wall extract from yeast (*Saccharomyces cerevisiae*) which is known to activate complement including $C_5a$. $C_5a$ is a chemotactic agent and activates granulocytes. The presence of leukocytes at zymosan treated sites in control animals, the reduction in leukocytes at zymosan sites in enlimomab treated animals, and the inhibition of zymosan-induced vascular permeability, suggests that this phenomenon is an ICAM-1 dependent granulocyte mediated inflammation. The data from the above-described analysis indicates that BIRR10 was as effective at inhibiting this granulocyte mediated injury as enlimomab.

EXAMPLE 14

Preparation of Monoclonal Antibody to ICAM-1

Immunization

A Balb/C mouse was immunized intraperitoneally (i.p.) with 0.5 mls of $2 \times 10^7$ JY cells in RPMI medium 103 days and 24 days prior to fusion. On day 4 and 3 prior to fusion, mice were immunized i.p. with $10^7$ cells of PMA differentiated U937 cells in 0.5 ml of RPMI medium.

Differentiation of U937 Cells

U937 cells (ATCC CRL-1593) were differentiated by incubating them at $5 \times 10^5$/ml in RPMI with 10% Fetal Bovine Serum, 1% glutamine and 50 mg/ml gentamycin (complete medium) containing 2 ng/ml phorbol-12-myristate acetate (PMA) in a sterile polypropylene container. On the third day of this incubation, one-half of the volume of medium was withdrawn and replaced with fresh complete medium containing PMA. On day 4, cells were removed, washed and prepared for immunization.

Fusion

Spleen cells from the immunized mice were fused with P3x63 Ag8.653 myeloma cells at a 4:1 ratio according to Galfre et al., (*Nature* 266:550 (1977)). After the fusion, cells were plated in a 96 well flat bottomed microtiter plates at $10^5$ spleen cells/well.

Selection for Anti-ICAM-I Positive Cells

After one week, 50 ml of supernatant were screened in the qualitative aggregation assay of Example 2 using both JY and SKW-3 as aggregating cell lines. Cells from supernatants inhibiting JY cell aggregation but not SKW-3 were selected and cloned 2 times utilizing limiting dilution. This experiment resulted in the identification and cloning of three separate hybridoma lines which produced anti-ICAM-1 monoclonal antibodies. The antibodies produced by these hybridoma lines were $IgG_{2a}$, $IgG_{2b}$, and IgM, respectively. The hybridoma cell line which produced the $IgG_{2a}$ anti-ICAM-1 antibody was given the designation R6.5.D6.E9.B2. The antibody produced by the preferred hybridoma cell line was designated R6.5.D6.E9.B2 (herein referred to as "R6-5-D6"). Hybridoma cell line R6.5.D6.E9.B2 was deposited with the American Type Culture Collection on Oct. 30, 1987 and given the designation ATCC HB 9580.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A homogeneous species of a poly(ethylene) glycol-modified derivative of an anti-ICAM-1 antibody capable of binding to ICAM-1, and of inhibiting ICAM1-mediated cellular adhesion, said homogeneous species having a defined and uniform degree of poly(ethylene) glycol-modification, and being substantially free of antibodies having different degrees of poly(ethylene) glycol-modification.

2. The homogeneous species of the poly(ethylene) glycol-modified derivative of the anti-ICAM-1 antibody of claim 1, wherein said antibody is a monoclonal antibody.

3. The homogeneous species of the poly(ethylene) glycol-modified derivative of the anti-ICAM-1 antibody of claim 1, wherein said derivative contains from 2 to 15 molecules of a monofunctional poly(ethylene) glycol.

4. The poly(ethylene) glycol-modified derivative of the anti-ICAM-1 antibody of claim 3, wherein said monofunctional poly(ethylene) glycol is an N-hydroxysuccinimidyl ester of poly(ethylene) glycol succinate.

5. The poly(ethylene) glycol-modified derivative of the anti-ICAM-1 antibody of claim 3, wherein said monofunctional poly(ethylene) glycol is an N-hydroxysuccinimidyl ester of poly(ethylene) glycol propionic acid.

6. The homogeneous species of the poly(ethylene) glycol-modified derivative of the anti-ICAM-1 antibody of claim 2, wherein said antibody is either (A) antibody enlimomab or (B) an antibody that binds ICAM-1 and that competitively inhibits the binding of enlimomab to ICAM-1.

7. The homogeneous species of the poly(ethylene) glycol-modified derivative of the anti-ICAM-1 antibody of claim 6, wherein said antibody is antibody enlimomab.

8. The homogeneous species of the poly(ethylene) glycol-modified derivative of the anti-ICAM-1 antibody of claim 1, wherein said derivatized antibody retains at least about 20% of the ability of a native anti-ICAM-1 antibody to bind ICAM-1.

9. The homogeneous species of the poly(ethylene) glycol-modified derivative of the anti-ICAM-1 antibody of claim 1, wherein said derivative has an in vivo serum half life that is greater than that of the non-poly(ethylene)glycol modified form of said antibody.

10. The homogeneous species of the poly(ethylene) glycol-modified derivative of the anti-ICAM-1 antibody of claim 8, wherein said antibody is antibody BIRR10.

11. The homogeneous species of the poly(ethylene) glycol-modified derivative of the anti-ICAM-1 antibody of claim 1, wherein said derivative is produced by a process comprising:

(a) incubating an anti-ICAM-1 antibody in the presence of an activated poly(ethylene) glycol molecule under conditions sufficient to permit the formation of said poly(ethylene) glycol-modified derivative of said antibody;

(b) subjecting said formed derivative to hydrophobic interaction chromatography under conditions sufficient to permit the separation of poly(ethylene) glycol modified antibody from non-poly(ethylene) glycol modified antibody; and (c) recovering said formed poly(ethylene) glycol modified antibody derivative from said hydrophobic interaction chromatography.

12. A pharmaceutical composition that comprises a single homogeneous species of a poly(ethylene) glycol-modified derivative of an anti-ICAM-1 antibody, wherein said antibody is capable of binding to ICAM-1, and of inhibiting ICAM-1-mediated cellular adhesion, said homogeneous species having a defined and uniform degree of poly(ethylene) glycol-modification, and being substantially free of antibodies having different degrees of poly(ethylene) glycol-modification.

13. The pharmaceutical composition of claim 12, wherein said poly(ethylene) glycol of said derivative is a monofunctional poly(ethylene) glycol.

14. The pharmaceutical composition of claim 12, wherein said anti-ICAM-1 antibody is either (A) antibody enlimomab or (B) an antibody that binds ICAM-1 and that competitively inhibits the binding of enlimomab to ICAM-1.

15. The pharmaceutical composition of claim 14, wherein said anti-ICAM-1 antibody is antibody enlimomab.

16. The pharmaceutical composition of claim 12, wherein said poly(ethylene) glycol-modified derivative of said anti-ICAM-1 antibody retains at least about 20% of the ability of a native anti-ICAM-1 antibody to bind ICAM-1.

17. The pharmaceutical composition of claim 12, wherein said poly(ethylene) glycol-modified derivative of said anti-ICAM-1 antibody has an in vivo serum half life that is greater than that of the non-poly(ethylene) glycol-modified form of said antibody.

18. The pharmaceutical composition of claim 12, wherein said poly(ethylene) glycol-modified derivative of said anti-ICAM-1 antibody is antibody BIRR10.

19. The pharmaceutical composition of claim 12, which additionally contains a physiologically acceptable carrier, excipient, or stabilizer.

20. The pharmaceutical composition of claim 13, wherein said derivative contains from 2 to 15 molecules of said monofunctional poly(ethylene) glycol.

21. The pharmaceutical composition of claim 20, wherein said monofunctional poly(ethylene) glycol is an N-hydroxysuccinimidyl ester of poly(ethylene) glycol succinate.

22. The pharmaceutical composition of claim 20, wherein said monofunctional poly(ethylene) glycol is an N-hydroxysuccinimidyl ester of poly(ethylene) glycol propionic acid.

23. The pharmaceutical composition of claim 12, wherein said derivative has an in vivo serum half life that is greater than that of the non-poly(ethylene)glycol modified form of said antibody.

24. A pharmaceutical composition that comprises two or more discreet homogeneous species of a poly(ethylene) glycol-modified derivative of an anti-ICAM-1 antibody, wherein the antibody of each such species is capable of binding to ICAM-1, and of inhibiting ICAM-1-mediated cellular adhesion, and wherein each of said homogeneous species has a defined and uniform degree of poly(ethylene) glycol-modification, and wherein said composition is substantially free of antibodies having different degrees of poly(ethylene) glycol-modification.

25. The pharmaceutical composition of claim 24, which additionally contains a physiologically acceptable carrier, excipient, or stabilizer.

26. The pharmaceutical composition of claim 24, wherein said composition contains species of poly(ethylene) glycol-modified anti-ICAM-1 antibody having different in vivo serum half lives.

27. The pharmaceutical composition of claim 24, wherein said poly(ethylene) glycol of said derivative is a monofunctional poly(ethylene) glycol.

28. The pharmaceutical composition of claim 27, wherein the average number of poly(ethylene) glycol derivatives per antibody possessed by said composition is from 2 to 15 molecules of a monofunctional poly(ethylene) glycol per antibody.

29. The pharmaceutical composition of claim 27, wherein said monofunctional poly(ethylene) glycol is an N-hydroxysuccinimidyl ester of poly(ethylene) glycol succinate.

30. The pharmaceutical composition of claim 27, wherein said monofunctional poly(ethylene) glycol is an N-hydroxysuccinimidyl ester of poly(ethylene) glycol propionic acid.

31. The pharmaceutical composition of claim 24, wherein at least one of said derivatives of said composition has an in vivo serum half life that is greater than that of the non-poly(ethylene) glycol-modified form of said antibody.

* * * * *